(12) United States Patent
Rabadan et al.

(10) Patent No.: US 9,422,342 B2
(45) Date of Patent: Aug. 23, 2016

(54) RECODING METHOD THAT REMOVES INHIBITORY SEQUENCES AND IMPROVES HIV GENE EXPRESSION

(75) Inventors: Raul Rabadan, Princeton, NJ (US); Michael Krasnitz, Princeton, NJ (US); Harlan Robins, Seattle, WA (US); Daniela Witten, Princeton, NJ (US); Arnold Levine, Doylestown, PA (US)

(73) Assignee: Institute of Advanced Study, Princeton, NJ (US)

( * ) Notice: Subject to any disclaimer, the term of this patent is extended or adjusted under 35 U.S.C. 154(b) by 1191 days.

(21) Appl. No.: 12/373,605

(22) PCT Filed: Jul. 12, 2007

(86) PCT No.: PCT/US2007/015877
§ 371 (c)(1),
(2), (4) Date: Nov. 16, 2009

(87) PCT Pub. No.: WO2008/091283
PCT Pub. Date: Jul. 31, 2008

(65) Prior Publication Data
US 2010/0203081 A1    Aug. 12, 2010

Related U.S. Application Data

(60) Provisional application No. 60/830,498, filed on Jul. 13, 2006, provisional application No. 60/906,611, filed on Mar. 13, 2007.

(51) Int. Cl.
| | |
|---|---|
| *C12N 7/00* | (2006.01) |
| *C07K 14/005* | (2006.01) |
| *A61K 39/21* | (2006.01) |
| *A61K 39/12* | (2006.01) |
| *A61K 39/00* | (2006.01) |

(52) U.S. Cl.
CPC .............. *C07K 14/005* (2013.01); *A61K 39/12* (2013.01); *A61K 39/21* (2013.01); *C12N 7/00* (2013.01); *A61K 2039/525* (2013.01); *A61K 2039/5252* (2013.01); *A61K 2039/5254* (2013.01); *A61K 2039/53* (2013.01); *C12N 2740/16021* (2013.01); *C12N 2740/16122* (2013.01); *C12N 2740/16134* (2013.01); *C12N 2740/16222* (2013.01); *C12N 2740/16234* (2013.01)

(58) Field of Classification Search
CPC .......... C12N 7/00; C12N 2740/16011; C12N 2740/16034; A61K 39/12
See application file for complete search history.

(56) References Cited

U.S. PATENT DOCUMENTS

| | | | |
|---|---|---|---|
| 6,733,994 B2 | 5/2004 | Weiner et al. | |
| 6,787,351 B2 | 9/2004 | Chen et al. | |
| 6,794,498 B2 | 9/2004 | Pavlakis et al. | |
| 6,958,226 B1 | 10/2005 | Gray et al. | |
| 2003/0092145 A1 | 5/2003 | Jira et al. | |

FOREIGN PATENT DOCUMENTS

| | | |
|---|---|---|
| JP | 02-013391 | 1/1990 |
| JP | 2002-533124 A | 10/2002 |
| WO | WO-98/22596 A1 | 5/1998 |
| WO | WO-00/39302 A2 | 7/2000 |
| WO | WO-2004/003153 A2 | 1/2004 |
| WO | WO2004016280 | 2/2004 |
| WO | WO-2007/139584 | 12/2007 |

OTHER PUBLICATIONS

Kotsopoulou, E., et al., May 2000, A rev-independent human immunodeficiency virus type 1 (HIV-1)-based vector that exploits a codon-optimized HIV-1 gag-pol gene, J. Virol. 74(10):4839-4852.*
Huang, W., et al., Jun. 2008, Coreceptor tropism can be influenced by amino acid substitutions in the gp41 transmembrane subunit of human immunodeficiency virus type 1 envelope protein, J. Virol. 82(11):5584-5593.*
Inubushi, R., et al., 1998, Suppression of HIV replication by dominant negative mutants of HIV-1 (Review), Intl. J. Mol. Med. 2:325-330.*
von Schwedler, U. K., et al., May 2003, Functional surfaces of the human immunodeficiency virus type 1 capsid protein, J. Virol. 77(9):5439-5450.*
International Search Report and Written Opinion issued for International Patent Application No. PCT/US2007/015877, Nov. 25, 2009.
Japanese Office Action (English translation) issued for Japanese Patent Application No. 2009-519523, dated Feb. 5, 2013, 2 pages.
Schneider, Ralf, et al., "Inactivation of the Human Immunodeficiency Virus Type 1 Inhibitory Elements Allow Rev-Independent Expression of Gag and Gag/Protease and Particle Formation", Journal of Virology, Jul. 1997, vol. 71, No. 7, pp. 4892-4903.
Huang, Y. et al., "A Recording Method to Improve the Humoral Immune Response to an HIV DNA Vaccine," PLoS ONE, Sep. 2008, vol. 3, Issue 9, e3214, pp. 1-4.
Schneider, R. et al., "Inactivation of the human immunodeficiency virus type 1 inhibitory elements allows rev-independent expression of gag and gag/protease and particle formation," Journal of Virology, vol. 71, No. 7, Jul. 1, 1997, pp. 4892-4903.

(Continued)

*Primary Examiner* — Jeffrey Parkin
(74) *Attorney, Agent, or Firm* — Wilmer Cutler Pickering Hale and Dorr LLP

(57) ABSTRACT

The invention relates to inhibitory nucleotide signal sequences or "INS" sequences in the genomes of lentiviruses. In particular the invention relates to the AGG motif present in all viral genomes. The AGG motif may have an inhibitory effect on a virus, for example by reducing the levels of, or maintaining low steady-state levels of, viral RNAs in host cells, and inducing and/or maintaining in viral latency. In one aspect, the invention provides vaccines that contain, or are produced from, viral nucleic acids in which the AGG sequences have been mutated. In another aspect, the invention provides methods and compositions for affecting the function of the AGG motif, and methods for identifying other INS sequences in viral genomes.

13 Claims, 4 Drawing Sheets

(56) References Cited

OTHER PUBLICATIONS

Figure 3:
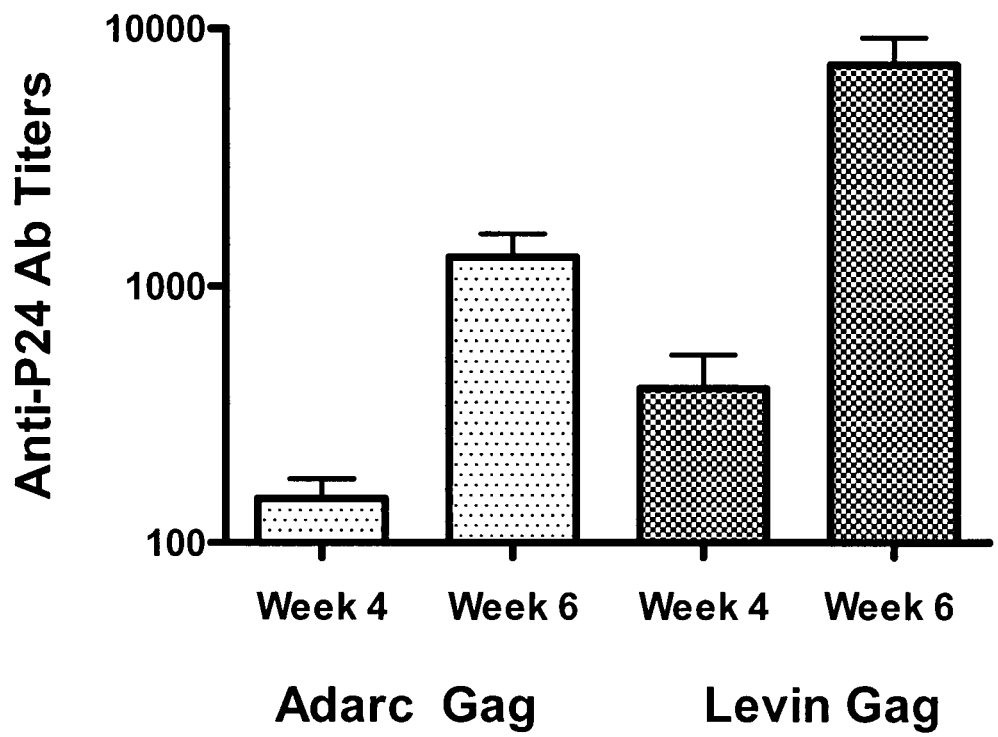

Korman, A. et al., "HIV-1 gag expression is quantitatively dependent on the ratio of native and optimized codons," Citologia, Nauka, St. Petersburg, RU, vol. 45, No. 1, 2003, pp. 86-93.
Supplementary European Search Report and Opinion issued for corresponding European Patent Application No. 07872545 mailed Nov. 25, 2009.
Partial European search report issued for EP Application No. 12160807.9, mailed May 16, 2012, 7 pages.
Ren, Hongzu, et al., "A Single-Stranded DNA Binding Site in the Human A1 Adenosine Receptor Gene Promoter", Molecular Pharmacology, 1998, vol. 53, pp. 43-51.
Extended European search report issued for EP Application No. 12160808.7, dated May 22, 2012, 9 pages.
Zur Megede, Jan, et al., "Increased Expression and Immunogenicity of Sequence-Modified Human Immunodeficiency Virus Type 1 *gag* Gene", Journal of Virology, Mar. 2000, vol. 74, No. 6, pp. 2628-2635.
Robins, Harlan, et al., "A Relative-Entropy Algorithm for Genomic Fingerprinting Captures Host-Phase Similarities", Journal of Bacteriology, Dec. 2005, vol. 187, No. 24, pp. 8370-8374.
Japanese Office Action issued by the Japan Patent Office for Japanese Application No. 2013-140710 dated Aug. 12, 2014 (7 pages).
Japanese Office Action issued by the Japan Patent Office for Japanese Application No. 2013-140710 dated Aug. 18, 2015 (7 pages).
Office Action from Japanese Patent Office for Japanese Application No. 2009-519523 dated Jul. 14, 2015, 14 pages (including English translation).
Examiner's First Report mailed Jan. 12, 2012 for corresponding Australian Patent Application No. 2007345319 (3 pages).
Office Action mailed by European Patent Office on Feb. 13, 2012 for corresponding European Application No. 07 872 545.4 (6 pages).
Kotsopoulou, E. et al., "A Rev-Independent Human Immunodeficiency Virus Type 1 (HIV-1)-Based Vector That Exploits a Codon-Optimized HIV-1 gag-pol Gene," Journal of Virology, May 2000, vol. 74, No. 10, p. 4839-4852.
Wang, S. et al., "Relative contributions of codon usage, promoter effciency and leader sequence to the antigen expression and immunogenicity of HIV-1 Env DNA vaccine," Vaccine 24 (2006)4531-4540.
Graf M et al. Concerted action of multiple cis-acting sequences is required for Rev dependence of late human immunodeficiency virus type 1 gene expression. J Virol. Nov. 2000;74(22):10822-6.
Office Action mailed on Apr. 5, 2016 for co-pending Japanese Application No. 2009-519523; 7 pages.
Comments on Pretrial Examination Report dated Jun. 1, 2016 for co-pending Japanese application No. 2013-140710; 2 pages.

\* cited by examiner

```
  1 atgggtgcgagagcgtcggtattaagcgggggagaattagataaatgggaaaaaattcgg
    M   G   A   R   A   S   V   L   S   G   G   E   L   D   K   W   E   K   I   R A   C                                                              A
 61 ttaAGGccAGGgggaaagaaacaatataaactaaaacatatagtatgggcaagcAGGgag
    L   R   P   G   G   K   K   Q   Y   K   L   K   H   I   V   W   A   S   R   E 121 ctagaacgattcgcagttaatcctggccttttagagacatcagaAGGctgtagacaaata
    L   E   R   F   A   V   N   P   G   L   L   E   T   S   E   G   C   R   Q   I G
181 ctgggacagctacaaccatcccttcagacAGGatcagaagaacttagatcattatataat
    L   G   Q   L   Q   P   S   L   Q   T   G   S   E   E   L   R   S   L   Y   N A                           A
241 acaatagcagtcctctattgtgtgcatcaaAGGatagatgtaaaagacaccaAGGaagcc
    T   I   A   V   L   Y   C   V   H   Q   R   I   D   V   K   D   T   K   E   A A                           A
301 ttagataagatagAGGaagagcaaaacaaaagtaagaaaaAGGcacagcaagcagcagct
    L   D   K   I   E   E   E   Q   N   K   S   K   K   K   A   Q   Q   A   A   A G              A
361 gacacAGGaaacaacagccAGGtcagccaaaattaccctatagtgcagaacctccAGGgg
    D   T   G   N   N   S   Q   V   S   Q   N   Y   P   I   V   Q   N   L   Q   G A
421 caaatggtacatcAGGccatatcacctagaactttaaatgcatgggtaaaagtagtagaa
    Q   M   V   H   Q   A   I   S   P   R   T   L   N   A   W   V   K   V   V   E A
481 gagaAGGctttcagcccagaagtaatacccatgttttcagcattatcagaAGGagccacc
    E   K   A   F   S   P   E   V   I   P   M   F   S   A   L   S   E   G   A   T 541 ccacaagatttaaataccatgctaaacacagtggggggacatcaagcagccatgcaaatg
    P   Q   D   L   N   T   M   L   N   T   V   G   G   H   Q   A   A   M   Q   M A                                              G
601 ttaaaagagaccatcaatgAGGaagctgcagaatgggatagattgcatccagtgcatgcA
    L   K   E   T   I   N   E   E   A   A   E   W   D   R   L   H   P   V   H   A G                          C                      G
661 GGgcctattgcaccAGGccagatgagagaaccaAGGggaagtgacatagcAGGaactact
    G   P   I   A   P   G   Q   M   R   E   P   R   G   S   D   I   A   G   T   T A           T                                  G
721 agtacccttcAGGaacaaatAGGatggatgacacataatccacctatcccagtAGGagaa
    S   T   L   Q   E   Q   I   G   W   M   T   H   N   P   P   I   P   V   G   E
```

Figure 1A

```
781 atctataaaagatggataatcctgggattaaataaaatagtaagaatgtatagccctacc
     I  Y  K  R  W  I  I  L  G  L  N  K  I  V  R  M  Y  S  P  T A
841 agcattctggacataagacaAGGaccaaAGGaaccctttagagactatgtagaccgattc
     S  I  L  D  I  R  Q  G  P  K  E  P  F  R  D  Y  V  D  R  F A
901 tataaaactctaagagccgagcaagcttcacaagAGGtaaaaaattggatgacagaaacc
     Y  K  T  L  R  A  E  Q  A  S  Q  E  V  K  N  W  M  T  E  T G
961 ttgttggtccaaaatgcgaacccagattgtaagactattttaaaagcattgggaccAGGa
     L  L  V  Q  N  A  N  P  D  C  K  T  I  L  K  A  L  G  P  G 1021 gcgacactagaagaaatgatgacagcatgtcAGGgagtggggggacccggccataaagca
      A  T  L  E  E  M  M  T  A  C  Q  G  V  G  G  P  G  H  K  A G
1081 agagttttggctgaagcaatgagccaagtaacaaatccagctaccataatgatacagaaA
      R  V  L  A  E  A  M  S  Q  V  T  N  P  A  T  I  M  I  Q  K C                                              G
1141 GGcaattttAGGaaccaaagaaagactgttaagtgtttcaattgtggcaaagaAGGgcac
      G  N  F  R  N  Q  R  K  T  V  K  C  F  N  C  G  K  E  G  H C        A  G                     A  G
1201 atagccaaaaattgcAGGgcccctAGGaaaaAGGgctgttggaaatgtggaaAGGaAGGa
      I  A  K  N  C  R  A  P  R  K  K  G  C  W  K  C  G  K  E  G A           G
1261 caccaaatgaaagattgtactgagagacAGGctaattttttAGGgaagatctggccttcc
      H  Q  M  K  D  C  T  E  R  Q  A  N  F  L  G  K  I  W  P  S A  G
1321 cacaAGGgaAGGccAGGgaatttcttcagagcagaccagagccaacagccccaccagaa
      H  K  G  R  P  G  N  F  L  Q  S  R  P  E  P  T  A  P  P  E A                                       G
1381 gagagcttcAGGgtttggggaagagacaacaactccctctcagaagcAGGagccgatagac
      E  S  F  R  F  G  E  E  T  T  T  P  S  Q  K  Q  E  P  I  D A
1441 aAGGaactgtatcctttagcttccctcagatcactctttggcagcgacccctcgtcacaa
      K  E  L  Y  P  L  A  S  L  R  S  L  F  G  S  D  P  S  S  Q 1501 taa
```

Figure 1B

| Vaccine Constructs | Exp 1 0.5 µg @ 48h | Exp 2 1 µg @ 48h | Exp 3 0.5 µg @ 72h | Exp 4 0.5 µg @ 48h |
|---|---|---|---|---|
| RK Gag | 3.56 (± 0.15) | 4.93 (± 0.25) | 4.70 (± 0.36) | 5.70 (± 0.36) |
| Adarc Gag | 2.26 (± 0.41) | 2.90 (± 0.52) | 2.63 (± 0.40) | 3.33 (± 0.40) |

Figure 2

RECODING METHOD THAT REMOVES INHIBITORY SEQUENCES AND IMPROVES HIV GENE EXPRESSION

The present application is a U.S. national phase application under 35 U.S.C. §371 of International Patent Application No. PCT/US2007/015877, filed Jul. 12, 2007, which claims priority to U.S. provisional patent application Ser. No. 60/830,498, filed on Jul. 13, 2006, and U.S. provisional patent application Ser. No. 60/906,611, filed on Mar. 13, 2007. All publications, patent applications, patents, and other references mentioned herein are incorporated by reference in their entirety.

The invention was made with government support by U.S. Department of Energy Grant U.S. DE-FG02-90ER40542. Accordingly, the U.S. Government may have certain rights in this invention.

BACKGROUND OF THE INVENTION

Lentiviruses belong to the Retrovirus family of viruses. The term "lenti" is Latin for "slow". Lentiviruses are characterized by having a long incubation period and the ability to infect neighboring cells directly without having to form extracellular particles. Their slow turnover, coupled with their ability to remain intracellular for long periods of time, make lentiviruses particularly adept at evading the immune response in infected subjects. Lentiviruses include immunodeficiency viruses, such as human immunodeficiency virus (HIV), simian immunodeficiency virus (SIV), feline immunodeficiency virus (FIV), and equine infectious anemia viruses (EIAV). Lentivirus infection can cause serious illness, and, if left untreated, can be fatal. In recent years several anti-retroviral drugs and drug cocktails that reduce viral load and ameliorate the symptoms of HIV infection have been developed. However, despite their successes, these drugs generally fail to eradicate the viral infection altogether. Instead the virus persists, often in a latent state, in infected subjects. There have also been multiple attempts to generate vaccines against lentiviral diseases such as HIV. However, to date, no vaccine is commercially available. Thus, there exists a need in the art to develop new drugs and vaccines against lentiviruses such as HIV.

SUMMARY OF THE INVENTION

The present invention provides a trinucleotide sequence motif, AGG, which is over-represented in the genome of the HIV virus relative to comparable genes in the human genome. The AGG motif is also present at high levels in the genomes of other viruses. The AGG motif is believed to be an inhibitory nucleotide signal sequence or and "INS" sequence.

In one embodiment, the present invention is directed to a virus nucleic acid that has been mutated to change one or more AGG sequences to a non-AGG sequence. In some embodiments, the virus nucleic is from an HIV virus. In other embodiments, the virus nucleic acid that has been mutated to change one or more AGG sequences to a non-AGG sequence is in the either the gag, pol, or env genes.

In another embodiment, the present invention is directed to a method for producing a virus nucleic acid having one or more AGG sequences mutated, comprising providing a virus nucleic acid containing one or more AGG sequences and changing one or more of the AGG sequences to a non-AGG sequence. The AGG sequence may be located in, or derived from, any location in the virus genome, including coding and non-coding regions. In another embodiment, if the AGG sequence is in a region of the virus nucleic acid that encodes a protein, the non-AGG sequence to which the AGG sequence is changed is selected such that it does not adversely affect the sequence, structure, function or immunogenicity of the protein encoded by the virus nucleic acid. In further embodiments, the virus nucleic acid is an HIV nucleic acid.

In another embodiment, the present invention is directed to a mutant virus having a genome that been mutated to change one or more AGG sequences to a non-AGG sequence. In some embodiments, the mutant virus is a mutant HIV virus.

In yet another embodiment, the present invention is directed to a recombinant virus that is not a virus but that contains a virus nucleic acid sequence that has been mutated to change one or more AGG sequences to a non-AGG sequence. In another embodiment, the mutant virus nucleic acid is a mutant HIV nucleic acid.

In a further embodiment, the present invention is directed to a virus protein expressed from a mutant virus nucleic acid sequence that has been mutated to change one or more AGG sequences to a non-AGG sequence. In another embodiment, the invention is directed to an HIV protein expressed from a mutant HIV nucleic acid sequence that has been mutated to change one or more AGG sequences to a non-AGG sequence.

In another embodiment, the present invention is directed to a virus vaccine comprising a virus nucleic acid sequence that has been mutated to change one or more AGG sequences to a non-AGG sequence. In another embodiment, the invention is directed to an HIV vaccine comprising an HIV nucleic acid sequence that has been mutated to change one or more AGG sequences to a non-AGG sequence.

In another embodiment, the present invention is directed to a virus vaccine comprising any of the virus nucleic acid sequences described above, including a virus nucleic acid sequence that has fewer AGG motifs than are found in a nucleic acid sequence of a naturally occurring virus. In another embodiment, the present invention is directed to an HIV vaccine comprising an HIV nucleic acid sequence that has fewer AGG motifs than would be found in a nucleic acid sequence of the corresponding naturally occurring HIV strain.

In another embodiment, the present invention is directed to a virus vaccine capable of higher protein expression than the corresponding wild-type virus, wherein the virus vaccine comprises a nucleic acid sequence with fewer AGG sequences than the wild-type virus nucleic acid sequence. In another embodiment, the present invention is directed to an HIV vaccine capable of higher protein expression than the corresponding wild-type HIV virus, wherein the HIV vaccine comprises a nucleic acid sequence with fewer AGG sequences than the wild-type HIV virus nucleic acid sequence.

In another embodiment, the present invention is directed to a virus vaccine comprising a protein produced from a virus nucleic acid that has been mutated to change one or more AGG sequences to a non-AGG sequence. In another embodiment, the present invention is directed to an HIV vaccine comprising a protein produced from an HIV nucleic acid that has been mutated to change one or more AGG sequences to a non-AGG sequence.

In another embodiment, the invention is directed to a composition comprising a vaccine as provided by the present invention, and an additional component selected from the group consisting of pharmaceutically acceptable diluents, carriers, excipients and adjuvants.

In yet another embodiment, the invention is directed to a method for immunizing a subject against a virus comprising administering to the subject an effective amount of a vaccine of present invention. In one embodiment, the invention is directed to a method for immunizing a subject against a virus, comprising administering to the subject an effective amount of a virus that has been mutated to change one or more AGG sequences to a non-AGG sequence. In another embodiment, the invention is directed to a method for immunizing a subject against HIV, comprising administering to the subject an effective amount of a nucleic acid encoding a virus protein that has been mutated to change one or more AGG sequences to a non-AGG sequence. In yet another embodiment, the invention is directed to a method for immunizing a subject against a virus, comprising administering to the subject an effective amount of a virus protein produced from a virus nucleic acid that has been mutated to change one or more AGG sequences to a non-AGG sequence. In some embodiments, the invention is directed to methods for immunizing a subject against HIV.

In another embodiment, the invention is directed to methods for identifying agents that inhibit or stimulate production of virus RNA, production of lentivirus protein or production of virus particles, or that inhibit or stimulate virus latency. In another embodiment, the method comprises providing a control cell containing at least one virus nucleic acid sequence containing at least one AGG motif, and a test cell containing at least one virus nucleic acid sequence containing at least one AGG motif that has been mutated to a non-AGG sequence, contacting the test cell and the control cell with one or more agents, and identifying at least one agent that inhibits or stimulates production of virus RNA, production of lentivirus protein or production of virus particles, or that inhibits or stimulates virus latency, in the test cell as compared to the control cell. In other embodiments, the agents inhibit or stimulate production of HIV RNA, production of HIV protein or production of HIV particles, or inhibit or stimulate HIV latency.

In another embodiment, the invention is directed to methods for identifying AGG motif binding agents. In another embodiment, the method comprises providing a control nucleic acid containing at least one AGG motif and a test nucleic acid containing at least one AGG motif that has been mutated to a non-AGG sequence, contacting the test nucleic acid and the control nucleic with one or more agents, and identifying at least one agent that binds to the control nucleic acid but does not bind the test nucleic acid, or that binds to the control nucleic acid with a higher affinity than it binds to the test nucleic acid.

In another embodiment, the invention is directed to an AGG motif binding agent, such as an AGG motif binding agent identified using one of the methods of the invention.

In yet another embodiment, the invention is directed to an agent that inhibits or stimulates binding of an AGG-binding agent to a nucleic acid containing at least one AGG motif, and to methods for identifying such agents.

The present invention is also directed to methods for identifying INS sequences other than the AGG motif in the genomes of viruses.

These and other embodiments of the invention are described further in the accompanying written description, drawings, and claims.

BRIEF DESCRIPTION OF THE DRAWINGS

FIG. 1, parts (a) and (b), shows the nucleotide sequence of the HIV-1 gag gene, and the amino acid sequence of the encoded protein. Part (a) shows nucleotide positions 1 to 780 and part (b) shows nucleotide positions 781 to 1543. The sequence contains 44 AGG motifs. Some of the possible mutations that can be made within these AGG motifs are illustrated above the nucleotide sequence. For example, the figure shows that the AGG motif starting at nucleotide position 1442 can be changed from AGG to AAG. FIG. 1 illustrates 38 AGG mutations.

FIG. 2 presents the results of Gag expression in transiently transfected 293 cells from four independent transfection experiments. The two different Gag sequences are the codon optimized version (Adarc) and the motif optimized version (RK) that we created. The RK version of the Gag gene has approximately two-fold higher expression than the codon optimized version.

FIG. 3 presents the immunogenicity of Gag DNA vaccines in mouse. The two different versions of Gag were made into DNA vaccines and injected into Balb/C mice, then boosted at four weeks. Anti-Gag antibody levels were measured by ELISA at the four week and six week time points. Our version, RK-Gag, induced an immune response that was five times larger than the codon optimized version at four weeks, which increased to a factor of 6 difference after six weeks.

DETAILED DESCRIPTION OF THE INVENTION

The present invention relates to inhibitory nucleotide signal sequences or "INS" sequences in viral genomes. The INS sequences of the invention may have an inhibitory effect on a virus, for example by reducing the levels of, or maintaining low steady-state levels of viral RNAs in host cells. The INS sequences of the invention may also play a role in viral latency. In one aspect, the present invention provides vaccines that contain, or are produced from, viral nucleic acids in which the INS sequences have been mutated. In another aspect, the present invention provides methods and compositions for affecting the function of INS sequences, and methods for identifying INS sequences. These and other embodiments are described herein.

Definitions

The singular forms "a," "an," and "the" include plural references unless the content clearly dictates otherwise. Thus, for example, reference to a "virus" includes a plurality of such viruses.

The terms "AGG", "AGG motif", "AGG sequence" and "AGG sequence motif" are used interchangeably herein to refer to a consecutive string of three nucleotides in a nucleic acid having the sequence AGG.

The term "mutant", as used herein refers to a modified nucleic acid or protein that has been altered by insertion, deletion and/or substitution of one or more nucleotides or amino acids. For example, the term mutant is used to refer to nucleic acid altered to disrupt an AGG motif, for example by substituting one or more nucleotides in the AGG motif with another nucleotide, or inserting one or more nucleotides to disrupt the AGG motif, or deleting one or more nucleotides in the AGG motif without substituting them for other nucleotides. Where the specification and claims refer to mutating an AGG motif to a non-AGG sequence, this encompasses substituting one or more nucleotides in the AGG motif with another nucleotide, or inserting one or more nucleotides to disrupt the AGG motif, or deleting one or more nucleotides from the AGG without substituting them for other nucleotides.

The term "wild type" or "WT" as used herein refers to nucleic acids, and to viruses, vectors, and cells containing nucleic acids, that have not been altered to disrupt an AGG motif. The term "wild type" also refers to proteins encoded by such nucleic acids. Thus, the term "wild type" includes naturally occurring nucleic acids, viruses, vectors, cells and proteins. However, in addition, the term "wild type" includes non-naturally occurring nucleic acids, viruses, cells and proteins. For example, unless otherwise stated, nucleic acids, viruses, vectors and cells that have been altered genetically are encompassed by the term "wild type" provided that those nucleic acids, viruses and cells have not been altered to disrupt an AGG motif therein.

As used herein, the term "homologue" refers to a nucleotide sequence sharing at least about 60%, about 70%, about 80%, about 90% or more identity with the nucleotide sequences referred to herein, such as the wild-type lentiviral nucleotide sequences referred to herein. The percent identity can be any number within the range of 60%-99.9%, inclusive.

The term "homologue" is also used to refer to proteins with amino acid sequences sharing at least about 60%, 70%, 80%, 90% or more identity with the amino acid sequences of the proteins referred to herein, such as the lentiviral proteins referred to herein. The percent identity can be any number within the range of 60%-99.9%, inclusive. In some embodiments, homologues of the proteins described herein have a substantially similar structure and/or function and/or immunogenicity to the wild type lentivirus proteins described herein.

As used herein, a "virus" includes any infectious particle having a protein coat surrounding an RNA or DNA core of genetic material. The term "virus", as used herein, also refers to all strains, isolates, and clades of all DNA and RNA viruses. Viruses include, but are not limited to all Adenoviruses, Alfamoviruses, Allexiviruses, Alloleviviruses, Alphacryptoviruses, Alphalipothrixviruses, Alphanodoaviruses, Alphapapillomaviruses, Alpharetroviruses, Alphaviruses, Amdoviruses, Ampeloviruses, Aphthoviruses, Aquabirnaviruses, Aquareoviruses, Arenaviruses, Arteriviruses, Ascoviruses, Asfiviruses, Atadenoviruses, Aureusviruses, Avastroviruses, Avenaviruses, Aviadenoviruses, Avibirnaviruses, Avihepadnaviruses, Avipoxviruses, Avulaviruses, Babuviruses, Badnaviruses, Barnaviruses, Bdellomicroviruses, Begomoviruses, Betacryptoviruses, Betalipothrixviruses, Betanodoviruses, Betapapillomaviruses, Betaretroviruses, Betatetraviruses, Bocaviruses, Bornaviruses, Bracoviruses, Brevidensoviruses, Bromoviruses, Bymoviruses, Capilloviruses, Capripoxviruses, Cardioviruses, Carlaviruses, Carmoviruses, Caulimoviruses, Cavemoviruses, Chlamydiamicroviruses, Chloroviruses, Chloriridoviruses, Chrysoviruses, Circoviruses, Closteroviruses, Coccolithoviruses, Coltiviruses, Comoviruses, Coronaviruses, Corticoviruses, Cripaviruses, Cucumoviruses, Curtoviruses, Cypoviruses, Cystoviruses, Cytomegaloviruses, Cytorhabdoviruses, Dainthoviruses, Deltapapillomaviruses, Deltaretroviruses, Densoviruses, Dependoviruses, Ebolaviruses, Enamoviruses, Enteroviruses, Entomobirnaviruses, Entomopoxviruses A, Entomopoxviruses B, Entomopoxviruses C, Ephemeroviruses, Epsilonpapillomaviruses, Epsilonretroviruses, Erboviruses, Errantiviruses, Erythroviruses, Etapapillomaviruses, Fabaviruses, Fijiviruses, Flaviviruses, Foveaviruses, Fuselloviruses, Gammalipothrixviruses, Gammapapillomaviruses, Gammaretroviruses, Giardiaviruses, Granuloviruses, Guttaviruses, Gyroviruses, Hantaviruses, Hemiviruses, Henipaviruses, Hepaciviruses, hepadnaviruses, Hepatoviruses, Hypoviruses, Ichnoviruses, Ictaluriviruses, Idnoreoviruses, Ilarviruses, Iltoviruses, Influenza A viruses, Influenza B viruses, Influenza C viruses, Inoviruses, Iotapapillomaviruses, Ipomoviruses, Iridoviruses, Isaviruses, Iteraviruses, Kappapapillomaviruses, Kobuviruses, Lagoviruses, Lambdapapillomaviruses, Leishmaniaviruses, Lentiviruses, Leporipoxviruses, Leviviruses, Luteoviruses, Lymphocryptoviruses, Lymphocystiviruses, Lyssaviruses, Machlomoviruses, Macluraviruses, Maculaviruses, Mamastroviruses, Mandariviruses, Marafiviruses, Marburgviruses, Mardiviruses, Marnaviruses, Mastadenoviruses, Mastreviruses, Megalocytiviruses, Metapneumoviruses, Metaviruses, Microviruses, Mitoviruses, Molluscipoxviruses, Morbilliviruses, Mupapillomaviruses, Muromegaloviruses, Mycoreoviruses, Nairoviruses, Nanoviruses, Narnaviruses, Necroviruses, Nepoviruses, Noroviruses, Novirhabdoviruses, Nucleopolyhedroviruses, Nucleorhabdoviruses, Nupapillomaviruses, Okaviruses, Oleaviruses, Omegatetraviruses, Omikronpapillomaviruses, Orbiviruses, Orthobunyaviruses, Orthohepadnaviruses, Orthopoxviruses, Orthoreoviruses, Oryzaviruses, Panicoviruses, Parapoxviruses, Parechoviruses, Partitiviruses, Parvoviruses, Pefudensoviruses, Pestiviruses, Petuviruses, Phaeoviruses, Phleboviruses, Phytoreoviruses, Pipapillomaviruses, Plasmaviruses, Plectrovi, Pneumoviruses, Poleroviruses, Polyomaviruses, Potexviruses, Potyviruses, Prasinoviruses, Prymnesioviruses, Pseudoviruses, Ranaviruses, Raphidoviruses, Respiroviruses, Rhadinoviruses, Rhinoviruses, Roseoloviruses, Rotaviruses, Rubiviruses, Rubulaviruses, Rudiviruses, Rymoviruses, Sapoviruses, Seadornaviruses, Sequiviruses, Siadenoviruses, Simplexviruses, Soymoviruses, Spiromicroviruses, Spumaviruses, Suipoxviruses, Tectiviruses, Teschoviruses, Thetapapillomaviruses, Thogotoviruses, Tombusviruses, Topocuviruses, Toroviruses, Tospoviruses, Totiviruses, Trichoviruses, Tritimoviruses, Tungroviruses, Tymoviruses, Varicelloviruses, Vesiculoviruses, Vesiviruses, Vitiviruses, Waikaviruses, Whispoviruses, Xipapillomaviruses, Yatapoxviruses, Zetapapillomaviruses or any combination thereof.

The term "retrovirus", as used herein, refers to all strains, isolates, and clades of all retroviruses including, but not limited to all alpharetroviruses, betaretroviruses, deltaretroviruses, epsilonretroviruses, gammaretroviruses, spumaviruses, and lentiviruses.

The term "lentivirus", as used herein, refers to all strains, isolates, and clades of all lentiviruses, including but not limited to, bovine immunodeficiency viruses, equine infectious anemia viruses (EIAV), feline immunodeficiency viruses (FIV), caprine arthritis encephalitis viruses, visna/maedi viruses, type 1 human immunodeficiency viruses (HIV-1), type 2 human immunodeficiency viruses (HIV-2) and simian immunodeficiency viruses (SIV).

The term "HIV", as used herein refers to all strains, isolates, and clades of both HIV-1 and HIV-2. Thus, unless stated otherwise, when the term HIV is used without specifying a type (i.e. without specifying type 1 or type 2) it is to be assumed that both HIV-1 and HIV-2 are referred to, including all strains, isolates, and clades of HIV-1 and HIV-2.

The terms "protein" and "peptide", as used herein, refer to polymeric chain(s) of amino acids. Although the term "peptide" is generally used to refer to relatively short polymeric chains of amino acids, and the term "protein" is used to refer to longer polymeric chain of amino acids, there is some overlap in terms of molecules that can be considered proteins and those that can considered peptides. Thus, the terms "protein" and "peptide" may be used interchangeably herein, and when such terms are used they are not intended to limit in anyway the length of the polymeric chain of amino acids referred to. Unless otherwise stated, the terms "protein" and "peptide" should be construed as encompassing all fragments, derivatives, variants, homologues, and mimetics of the specific proteins mentioned, and may comprise naturally occurring amino acids or synthetic amino acids.

The terms "vaccine" and "immunogenic composition" are used interchangeably herein to refer to agents or compositions capable of inducing an immune response against a virus. In another embodiment, the present invention provides vaccines capable of inducing an immune response against a lentivirus such as HIV-1, HIV-2, SIV, FIV or EIAV. The terms "vaccine" and "immunogenic composition" encompass prophylactic or preventive vaccines and therapeutic vaccines. The vaccine compositions of the invention may also be cross-reactive with, and effective against, multiple different viruses. For example, the immunogenic compositions of the invention may be cross-reactive with, and effective against, multiple different types of virus, lentivirus and/or multiple different types of immunodeficiency virus. Similarly, the immunogenic compositions of the invention may be cross-reactive between different strains and clades of the same virus. For example, an immunogenic composition according to the present invention that is effective against one strain of HIV may also be effective against multiple strains of HIV.

As used herein the terms "protein vaccine", "proteinaceous vaccine" and "subunit vaccine" are used interchangeably to refer to vaccines that contain a lentiviral or viral protein component.

The term "agent", as used herein, is used generically to refer to any molecule, such as a protein, peptide, or pharmaceutical, including but not limited to, agents that bind to AGG motifs, agents that inhibit the function of AGG motifs, agents that stimulate the function of AGG motifs, agents that inhibit or stimulate binding of another agent to an AGG motif, vaccines that contain or are made from nucleic acids having mutated AGG motifs, molecules that are co-administered with the vaccines of the invention, and the like.

The term "host" refers to any animal or cell type (including animal cells, bacterial cells, yeast cells, and insect cells) which may be infected by a virus, a lentivirus, or which may be used to grow, amplify, or express any of the vaccine strains, viruses, vectors, plasmids or proteins described herein.

The term "subject" as used herein, refers to any animal to whom a vaccine or agent according to the present invention may be administered, including humans and other mammalian species.

"Immunogenicity" includes the ability of a substance to stimulate an immune response. Immunogenicity is measured, for example, by determining the presence of antibodies specific for the substance. The presence of antibodies is detected by methods known in the art, for example an ELISA assay.

In one aspect, the invention is directed to viruses which have a reduced number of AGG sequences. In some embodiments, the present invention is directed to the lentiviruses. In other embodiments, the present invention is directed to the lentivirus HIV.

HIV Biology

The HIV genome encodes several proteins, some of which are produced as "poly-proteins" that produce different functional entities upon proteolytic cleavage. All of the proteins encoded by the HIV genome, including but not limited to "poly-proteins" and their proteolytic cleavage products, are within the scope of the invention, and may be referred to herein as "HIV proteins", "HIV peptides", HIV poly-proteins", "proteins of the invention", "polyproteins of the invention" or "peptides of the invention". The INSs of the invention may be present in the nucleotide sequences that encode any or all of these proteins. The INSs of the invention may also be present in non-coding regions of the HIV genome.

For example, the HIV genome encodes the pr55 GAG protein, which can be cleaved by a viral protease into p17MA, p24CA, p7 and p6 proteins that make up the core of the virus. The Pr160 GAG-POL precursor protein produces a polymerase poly-protein that is made by translational frame shifting and is subsequently cleaved into a reverse transcriptase (RT), RNAase H, a protease (PR) and an integrase (IN). The Gp160 envelope protein is cleaved by a cellular protease into a Gp120 protein (ENV) that attaches the virus to the CD-4 receptor and the co-receptor and a Gp41 trans-membrane protein that fuses the viral envelope into the host cell membrane. These are the major structural proteins and enzymes of the HIV particle. Two additional proteins, Tat and Rev, regulate the transcription of the integrated provirus (Tat) and the transport of unspliced mRNAs (GAG-POL and viral genomic RNA) from the nucleus to the cytoplasm (Rev). These activities regulate the expression of viral genes and the temporal events during the replication cycle. Four accessory proteins: Vpu, Vif, Vpr and NO are adaptors that form complexes with cellular proteins and enhance infectious virus production in vivo, but have more minimal phenotypes in some cell cultures. All of these HIV proteins are within the scope of the invention.

The HIV virus attaches to T-cells and monocytes using its gp120 ENV protein, which binds to the CD-4 protein and co-receptors at the cell surface. T-cells express the cytokine receptor CXCR4, monocytes express the CCR5 co-receptor, and peripheral blood lymphocytes express both. Genetic alterations in the ENV protein produce monocyte tropic viruses (R5 viruses), T-cell tropic viruses (X4 viruses) and dual tropic viruses. The co-receptor is essential for ENV attachment and Gp41 fusion. People who lack a normal HIV co-receptor, for example because they carry the CCR5/delta 32 polymorphism, are almost completely resistant to HIV infection. (See, for example, Deng et al., Nature (1996) Vol. 381, p 661-6 and Samson et al., Nature, (1996) Vol. 382 p 722-5). Drugs that block the CCR5 co-receptor are now in clinical trials.

After fusion of the HIV virus with the cell, the virus core particle copies the viral RNA into a DNA copy using reverse transcriptase (RT) and the particle moves to the nucleus where it integrates the viral DNA into the cellular genome using integrase (IN). The long terminal repeat (LTR) DNA sequences contain a number of transcription factor binding sites that are essential to produce viral mRNAs from the incorporated DNA. In addition to a TATA element, there are two NF kappa b sites and three Sp-1 sites in the LTR which are recognized by cellular transcription factors. In addition sites for LEF, ETS and USF transcription factors are also present. These cellular transcription factors help to initiate transcription, but this occurs at a very low level. After TAT is produced, it binds to a cellular protein (cyclin T1) and the TAT-cycT1 complex then binds to an RNA loop structure (called TAR) in the viral mRNA. The TAT-cycT1 complex next binds the CDK9 protein kinase, which phosphorylates the carboxy-terminal end of one of the subunits of RNA polymerase-II. This is required for the efficient initiation of viral RNA transcription (which increases by 100 fold). Over 30 different viral RNA molecules are produced by these events. They fall into three categories: (1) unspliced RNAs that are used to make GAG, POL and the intact viral genomes, (2) partially-spliced RNAs of about 5.0 Kb in size, that are employed to make ENV, Vif, Vpu, and Vpr proteins, and (3) small, spliced RNAs (1.7-2.0 Kb) that are translated into REV, TAT and Nef. The transport of these RNAs out of the nucleus is most efficient for the fully spliced mRNAs. Thus, early after infection, only TAT, REV and NEF are made efficiently. TAT binding to TAR then increases the rate of transcription by 100 fold. The larger, unspliced or poorly spliced mRNAs are transported into the cytoplasm more efficiently only after the REV protein is made and binds to the Rev-responsive element (RRE) in the ENV gene. In this way, the synthesis of TAT and REV regulate timing of the viral life cycle.

In addition to TAT, there is a second set of signals in the HIV genome that reduce the steady state levels of viral RNA in cells. These are referred to as inhibitory nucleotide signal sequences (INS sequences). Putative INS-containing regions have been identified previously in the gag/pol regions of the HIV genome (see Schneider et al., Journal of Virology, (1997), Vol. 71, p. 4892-4903). In the prior study by Schneider et al. the region containing putative INS sequences was mutated to eliminate AUUUA pentanucleotides and to decrease AU content without altering the coding capacity of the region. It was found that these mutations resulted in an increase in the level of HIV RNA by up to 70-130 fold. With the INS sequences mutated and in the presence of a functional REV, the increase in HIV RNA in an infected cell was 160 fold higher than without these two distinct functions.

It is believed that the HIV virus gains an advantage by having a low steady state level of viral RNA. It has been proposed that a virus that replicates rapidly and kills the cell rapidly produces less virus per-cell than one that employs a slower cycle. Indeed, rapid efficient virus production and cell killing, as is observed with polio viruses for example, often leads to complete immune clearance of the virus and immunity to subsequent infections. In contrast, viruses which remain intracellular for prolonged periods are able to evade, or at least reduce the effectiveness of, the immune response against them.

Although mutations in the putative INS-containing region of the gag/pol genes are additive, the sequence(s) of the INS have not been previously defined (Schneider et al.). The INS-containing region(s) acts to lower the steady state levels of viral RNA in an infected cell. At least three possible mechanisms exists including (1) a lowered rate of transcription, (2) an increased rate of RNA degradation of HIV RNA, (3) a lowered rate of transport of HIV RNA out of the nucleus (Schneider et al.)

Poor immune response to Env and Gag are a fundamental problem in the effort to create a vaccine for HIV-1. For a DNA vaccine, immune response is correlated with expression level, so an increase in expression of these ORFs could alleviate a significant road block to the construction of a viable vaccine. The large mRNAs from HIV have processing problems and are not efficiently exported from the nucleus, presumably due to a set of protein binding sites encoded in their RNA. Identifying and removing the signal which causes the nuclear confinement may significantly increase expression levels of these ORFs and improve the immune response.

The genome of human immunodeficiency virus type 1 (HIV-1) contains nine open reading frames (ORFs), all of which are expressed from a single promoter through alternative splicing. The splice forms for the six ORFs Gag, Pol, Env, Vpu, Vif, and Vpr, along with the full length mRNA, contain REV response elements (RREs) encoded in their RNA. In the absence of the REV protein, these six ORFs are poorly expressed. The remaining three ORFs, Tat, Rev, and Nef, are expressed efficiently independent of the REV protein.

The mRNAs which contain RREs likely also contain a yet undetermined signal or set of signals which prevents normal expression. A primary cause of the poor expression of these ORFs is nuclear confinement. The genome of HIV-1 has an anomalous nucleotide distribution as compared with the set of known coding genes in the human genome. The percent of Adenine averaged over clinical isolates of HIV-1 is above the mean human coding gene. Codon optimized strains, which are widely used in present experiments and vaccine trials, can increase the expression level of Gag transfected into human cells between 500 and 1000 fold. However, the substantial increase in expression due to codon optimization can, at best, indirectly address the problem of nuclear isolation.

The assembly of HIV virus particles takes place at the cell membrane where the GAG-POL poly-protein packages the viral RNA. The viral particles bud off from the plasma membrane of the host cell, which now contains the HIV ENV and gp41 proteins. After release of the virus particle the viral protease (PR) cleaves the GAG-POL poly-protein giving rise to mature and infectious particles. Vif is believed to be involved in assembly of the virus. Also, NEF and Vpu are involved in the degradation of cellular CD-4 protein and release of viruses from the membrane of infected cells. The Vpr protein is incorporated into the virion at assembly and appears to play a role early in infection, transporting the particle into the nucleus, while Vif antagonizes an anti-viral cellular enzyme activity in the cell. The released infectious virus attaches to and infects additional cells and the progressive infection and killing of CD-4 lymphocytes results in an incapacitated immune system.

The INS Sequences of the Invention

Because the genetic code is degenerate, nucleotide sequences can differ from each other at the nucleotide level but encode the same protein or peptide. However, in nature there is often selective pressure for particular codon usage and AT/GC content. There is also selective pressure for the frequency and order of amino acids in the proteins encoded by the nucleotide sequences. A method that normalizes for each of these selection pressures, and then calculates the average frequency of sequence motifs (for example, sequence motifs of 2-8 nucleotides in length) expected in a genome and compares this to the actual frequency of these motifs, has been developed. This method is described in co-pending provisional patent application No. 60/808,420, and also in Robins et al. (2005), Journal of Bacteriology, Vol. 187, p. 8370-74, the contents of which are hereby incorporated by reference. This method can be used to produce a list of over- and/or under-represented oligonucleotide sequence motifs in a genome. Such over- and/or under-represented sequences may contain functional information.

In the present invention, the method of Robins et al. was used to look for such over- and under-represented sequence motifs in the HIV-1 and human genomes. A sequence motif, AGG, was found to be over-represented in the HIV genome and under-represented in comparable human genes. For example, FIG. 1 shows 48 AGG motifs identified in the HIV-1 the gag gene. Over two thirds of the AGG motifs identified in the gag gene were not in the reading frame that encodes amino acids, suggesting that these sequences were not conserved due to selection at the amino acid/protein level. While third codon position changes are common in different HIV isolates, the AGG motif was also found to be particularly conserved even in the third position of codons. Furthermore, the AGG motif was found to be conserved in over 400 HIV-1 strains analyzed, and also in HIV-2 and in other lentiviruses including FIV, SIV, and EIAV.

It is possible that the INS sequences of the invention, such as the AGG sequence motif, may be present in the genome of many different types of viruses. In one embodiment, the present invention is directed to INS sequences in the genome of any virus family, including but not limited to, viruses of the Adenovirus, Alfamovirus, Allexivirus, Allolevivirus, Alphacryptovirus, Alphalipothrixvirus, Alphanodoavirus, Alphapapillomavirus, Alpharetrovirus, Alphavirus, Amdovirus, Ampelovirus, Aphthovirus, Aquabirnavirus, Aquareovirus, Arenavirus, Arterivirus, Ascovirus, Asfivirus, Atadenovirus, Aureusvirus, Avastrovirus, Avenavirus, Aviadenovirus, Avibirnavirus, Avihepadnavirus, Avipoxvirus, Avulavirus, Babuvirus, Badnavirus, Barnavirus, Bdellomicrovirus, Begomovirus, Betacryptovirus, Betalipothrixvirus, Betanodovirus, Betapapillomavirus, Betaretrovirus, Betatetravirus, Bocavirus, Bornavirus, Bracovirus, Brevidensovirus, Bromovirus, Bymovirus, Capillovirus, Capripoxvirus, Cardiovirus, Carlavirus, Carmovirus, Caulimovirus, Cavemovirus, Chlamydiamicrovirus, Chlorovirus, Chloriridovirus, Chrysovirus, Circovirus, Closterovirus, Coccolithovirus, Coltivirus, Comovirus, Coronavirus, Corticovirus, Cripavirus, Cucumovirus, Curtovirus, Cypovirus, Cystovirus, Cytomegalovirus, Cytorhabdovirus, Dainthovirus, Deltapapillomavirus, Deltaretrovirus, Densovirus, Dependovirus, Ebolavirus, Enamovirus, Enterovirus, Entomobirnavirus, Entomopoxvirus A, Entomopoxvirus B, Entomopoxvirus C, Ephemerovirus, Epsilonpapillomavirus, Epsilonretrovirus, Erbovirus, Errantivirus, Erythrovirus, Etapapillomavirus, Fabavirus, Fijivirus, Flavivirus, Foveavirus, Fusellovirus, Gammalipothrixvirus, Gammapapillomavirus, Gammaretrovirus, Giardiavirus, Granulovirus, Guttavirus, Gyrovirus, Hantavirus, Hemivirus, Henipavirus, Hepacivirus, hepadnavirus, Hepatovirus, Hypovirus, Ichnovirus, Ictalurivirus, Idnoreovirus, Ilarvirus, Iltovirus, Influenza A virus, Influenza B virus, Influenza C virus, Inovirus, Iotapapillomavirus, Ipomovirus, Iridovirus, Isavirus, Iteravirus, Kappapapillomavirus, Kobuvirus, Lagovirus, Lambdapapillomavirus, Leishmaniavirus, Lentivirus, Leporipoxvirus, Levivirus, Luteovirus, Lymphocryptovirus, Lymphocystivirus, Lyssavirus, Machlomovirus, Macluravirus, Maculavirus, Mamastrovirus, Mandarivirus, Marafivirus, Marburgvirus, Mardivirus, Marnavirus, Mastadenovirus, Mastrevirus, Megalocytivirus, Metapneumovirus, Metavirus, Microvirus, Mitovirus, Molluscipoxvirus, Morbillivirus, Mupapillomavirus, Muromegalovirus, Mycoreovirus, Nairovirus, Nanovirus, Narnavirus, Necrovirus, Nepovirus, Norovirus, Novirhabdovirus, Nucleopolyhedrovirus, Nucleorhabdovirus, Nupapillomavirus, Okavirus, Oleavirus, Omegatetravirus, Omikronpapillomavirus, Orbivirus, Orthobunyavirus, Orthohepadnavirus, Orthopoxvirus, Orthoreovirus, Oryzavirus, Panicovirus, Parapoxvirus, Parechovirus, Partitivirus, Parvovirus, Pefudensovirus, Pestivirus, Petuvirus, Phaeovirus, Phlebovirus, Phytoreovirus, Pipapillomavirus, Plasmavirus, Plectrovi, Pneumovirus, Polerovirus, Polyomavirus, Potexvirus, Potyvirus, Prasinovirus, Prymnesiovirus, Pseudovirus, Ranavirus, Raphidovirus, Respirovirus, Rhadinovirus, Rhinovirus, Roseolovirus, Rotavirus, Rubivirus, Rubulavirus, Rudivirus, Rymovirus, Sapovirus, Seadornavirus, Sequivirus, Siadenovirus, Simplexvirus, Soymovirus, Spiromicrovirus, Spumavirus, Suipoxvirus, Tectivirus, Teschovirus, Thetapapillomavirus, Thogotovirus, Tombusvirus, Topocuvirus, Torovirus, Tospovirus, Totivirus, Trichovirus, Tritimovirus, Tungrovirus, Tymovirus, Varicellovirus, Vesiculovirus, Vesivirus, Vitivirus, Waikavirus, Whispovirus, Xipapillomavirus, Yatapoxvirus or Zetapapillomavirus families.

In another embodiment, the present invention is directed to INS sequences in the genome of viruses of the retroviridae family. Examples of such viruses include, but are not limited to viruses of the alpharetrovirus, betaretrovirus, deltaretrovirus, epsilonretrovirus, gammaretrovirus, Spumavirus, and lentivirus genera.

In a further embodiment, the present invention is directed to INS sequences in the genome of lentivirus. Examples of such lentiviruses include, but are not limited to, bovine immunodeficiency viruses, equine infectious anemia viruses (EIAV), feline immunodeficiency viruses (FIV), caprine arthritis encephalitis viruses, visna/maedi viruses, human immunodeficiency virus 1 (HIV-1), human immunodeficiency virus 2 (HIV-2) and simian immunodeficiency virus (SIV).

The over-representation of the AGG motif, and its conservation across the lentivirus family, suggest that is functionally important. It is believed that the AGG sequence motif may be an INS sequence, and may have an inhibitory effect on the viruses that possess it. For example, it is believed that the AGG motif of the invention may be involved in any and all of the inhibitory effects generally attributed to INS sequences, including but not limited to maintaining a low steady state level of viral RNA, slow turnover of the virus, and possibly latency.

The discovery of the AGG motif provides new opportunities for vaccine production, production of recombinant viral proteins, identification of new drugs, and for studying viral latency, among other things. Such applications are described in more detail below.

In one embodiment, the present invention is directed to a lentiviral or viral nucleic acid, such as for example an HIV nucleic acid, that has been mutated to change one or more AGG sequences to a non-AGG sequence. In another embodiment, the present invention is directed to methods of making such mutations. Such mutations may be made anywhere in the genome of a lentivirus or a virus, including coding and non-coding regions. For example, in one embodiment, the mutations may be in the gag, pol, and/or env genes of a lentivirus genome. Such mutations may also be made in any nucleic acids derived from lentiviruses or viruses. The present invention encompasses any and all nucleic acids derived from a lentivirus or a virus which have been mutated to change one or more AGG sequences to a non-AGG sequence, and any and all methods of making such mutations, regardless of whether that nucleic acid is present in a virus, a vaccine strain, a plasmid, an expression vector, as a free nucleic acid molecule, or elsewhere.

The AGG motifs of the invention may be mutated to any non-AGG sequence by substituting one or more nucleotides in the AGG motif with another nucleotide. For example, the first nucleotide in an AGG motif may be mutated from an A to a G, T, C, U, or any other naturally occurring or synthetic nucleotide. The second nucleotide in an AGG motif may be mutated from a G to an A, T, C, U, or any other naturally occurring or synthetic nucleotide. The third nucleotide in an AGG motif may be mutated from a G to an A, T, C, U, or any other naturally occurring or synthetic nucleotide. Any one position of the AGG motif may be changed, or multiple positions of the AGG motif may be changed. For example, either nucleotide position 1, 2, or 3 in the AGG motif may be changed (where position 1 is the position that was originally an A, position 2 is the position that was originally a G, and position 3 is the position that was originally the second G). Furthermore, any two positions of the AGG motif may be changed as described above, or all three positions of the AGG motif may be changed as described above. Mutating an AGG motif to a non-AGG sequence also encompasses other types of mutations, such as inserting one or more nucleotides to disrupt the AGG motif, or deleting one or more nucleotides from the AGG without substituting them for other nucleotides.

The AGG motif to be changed may be located anywhere in any lentiviral, viral, lentivirus-derived or virus derived nucleic acid, for example in coding or non-coding regions. In embodiments where the AGG motif is located in a coding region, the AGG motif can be changed to a sequence that does not alter the amino acid(s) encoded by the nucleic acid. For example, in the event that the AGG motif constitutes a single codon, and thus encodes the amino acid arginine (Arg), the motif can be changed to either AGA, CGG, CGA, CGC, CGU, or CGT, each of which also encode arginine. It is possible that an AGG motif may span two codons in a coding region. If so, it is again possible, that the AGG motif if changed to a sequence that need not alter the amino acid(s) encoded by either of the two codons spanned by the AGG motif. One of skill in the art can readily determine how to change one or more of the nucleotide positions within an AGG motif without altering the amino acid(s) encoded, by referring to the genetic code, or to RNA or DNA codon tables.

In some embodiments the AGG motif may be changed to a non-AGG trinucleotide that does affect the amino acid(s) encoded. Such mutations may result in one or more different amino acids being encoded, or may result in one or more amino acids being deleted or added to the amino acid sequence. If the AGG motif is changed to a non-AGG trinucleotide that does affect the amino acid(s) encoded, it is possible to make one of more amino acid changes that do not adversely affect the structure, function or immunogenicity of the protein encoded. For example, the mutant protein encoded by the mutant nucleic acid can have substantially the same structure and/or function and/or immunogenicity as the wild-type protein. It is possible that some amino acid changes may lead to increased immunogenicity and artisans skilled in the art will recognize when such modifications are appropriate.

The mutations of AGG motifs to non-AGG motifs may be made by any suitable mutagenesis method known in the art, including, but are not limited to, site-directed mutagenesis, oligonucleotide-directed mutagenesis, positive antibiotic selection methods, unique restriction site elimination (USE), deoxyuridine incorporation, phosphorothioate incorporation, and PCR-based mutagenesis methods. Details of such methods can be found in, for example, Lewis et al. (1990) Nucl. Acids Res. 18, p 3439; Bohnsack et al. (1996) Meth. Mol. Biol. 57, p 1; Vavra et al. (1996) Promega Notes 58, 30; Altered Sites® II in vitro Mutagenesis Systems Technical Manual #TM001, Promega Corporation; Deng et al. (1992) Anal. Biochem. 200, p 81; Kunkel et al. (1985) Proc. Natl. Acad. Sci. USA 82, p 488; Kunke et al. (1987) Meth. Enzymol. 154, p 367; Taylor et al. (1985) Nucl. Acids Res. 13, p 8764; Nakamaye et al. (1986) Nucl. Acids Res. 14, p 9679; Higuchi et al. (1988) Nucl. Acids Res. 16, p 7351; Shimada et al. (1996) Meth. Mol. Biol. 57, p 157; Ho et al. (1989) Gene 77, p 51; Horton et al. (1989) Gene 77, p 61; and Sarkar et al. (1990) BioTechniques 8, p 404. Numerous kits for performing site-directed mutagenesis are commercially available, such as the QuikChange® II Site-Directed Mutagenesis Kit from Stratgene Inc. and the Altered Sites® II in vitro mutagenesis system from Promega Inc. Such commercially available kits may also be used to mutate AGG motifs to non-AGG sequences.

Vaccines

The methods and composition of the present invention may be particularly useful for the production of vaccines. The low amounts of viral particles produced during an infection cycle, coupled with their ability to remain intracellular for extended periods of time, limits the exposure of lentiviruses such as HIV to the immune system. This property is advantageous to the virus but adversely affects the ability to generate an effective vaccine. For example, viral vaccines that are designed to infect and replicate in host cells may produce low levels of progeny and remain "hidden" in host cells for extended periods of time. Consequently, such vaccines may not be able to effectively trigger an immune response and immunological memory. Similarly, DNA vaccines which encode one or more lentiviral or viral antigens are likely to express low levels of the antigen in the host, in turn limiting the effectiveness of the DNA vaccine in generating an immune response and immunological memory.

The discovery of the AGG motif of the present invention raises the possibility of generating mutant viruses that have fewer AGG motifs and therefore have increased steady state levels of viral RNA, increased expression of viral-encoded protein, increased infection cycles and increased exposure to the immune system. Such mutant viruses would be useful as viral vaccines. Vaccines that comprise, or are derived from, such mutant viruses are described in more detail below. The discovery of the AGG motif of the present invention also raises the possibility of generating mutant viral nucleic acid sequences that produce virally encoded proteins at a much higher rate, and/or in much larger quantities, than would otherwise be the case. Such mutant nucleic acids could be useful as DNA vaccines, as described in more detail below. Furthermore, such mutant nucleic acids could also be useful for production of viral proteins for use in protein vaccines. Vaccines that comprise, or are derived from, such proteins are also described in more detail below.

The present invention encompasses both prophylactic/preventive vaccines and therapeutic vaccines. A prophylactic vaccine is one administered to subjects who are not infected with the disease against which the vaccine is designed to protect. An ideal preventive vaccine will prevent a virus from establishing an infection in a vaccinated subject, i.e. it will provide complete protective immunity. However, even if it does not provide complete protective immunity, a prophylactic vaccine may still confer some protection to a subject. For example, a prophylactic vaccine may decrease the symptoms, severity, and/or duration of the disease. In the case of HIV, a prophylactic vaccine may prevent or delay the progression to full-blown AIDS even if it is not sufficient to provide complete protective immunity. A therapeutic vaccine, is administered to reduce the impact of a viral infection in subjects already infected with that virus. A therapeutic vaccine may decrease the symptoms, severity, and/or duration of the disease. In the case of HIV, administration of a therapeutic vaccine may prevent or delay the progression to full-blown AIDS.

The present invention encompasses any and all types of vaccine that comprise a nucleic acid having a mutated AGG motif, or that are produced from a nucleic acid having a mutated AGG motif. Several different types of vaccine are described herein. However, one of skill in the art will recognize that there are other types of vaccines that may be used, and other methods for producing vaccines. The present invention is not limited to the specific types of vaccines illustrated. Instead, it encompasses any and all vaccines that comprise a nucleic acid having a mutated AGG motif, or that are produced from a nucleic acid having a mutated AGG motif.

The present invention encompasses "viral vaccines". The term "viral vaccine" as used herein includes attenuated viral vaccines, inactivated viral vaccines and viral vector vaccines. The present invention also encompasses DNA vaccines and proteinaceous or "subunit" vaccines, each of which is described below. It should be noted that there is significant overlap among the various types of vaccines. For example, viral vaccines may comprise nucleic acids that are the same as, or similar to those used to make DNA vaccines. Similarly, DNA vaccines and viral vaccines may express proteins that are the same as, or similar to, those used to make proteinaceous vaccines. Thus, the description provided for any one type of vaccine below should not be construed as being useful for only that vaccine type. Instead all of the description regarding any one type of vaccine can be used and applied interchangeably to any and all of the types of vaccines encompassed by the present invention.

In certain aspects, the invention provides immunogenic compositions capable of inducing an immune response against viruses including the lentiviruses of the invention comprising SEQ ID NO: 1. In one embodiment, the immunogenic compositions are capable of ameliorating the symptoms of a lentiviral or viral infection and/or of reducing the duration of a lentiviral or viral infection. In another embodiment, the immunogenic compositions are capable of inducing protective immunity against virus infection. The immunogenic compositions of the invention can be effective against the lentiviruses disclosed herein, and may also be cross-reactive with, and effective against, multiple different clades and strains of lentiviruses, and against other viruses.

Viral Vaccines

A) Attenuated Viral Vaccines

In one embodiment, the invention provides attenuated viral vaccines having one or more AGG sequences mutated. Attenuated viruses are viruses that have been altered to weaken them, such that they no longer cause disease, but may still stimulate an immune response. There are many ways in which a virus may be attenuated. For example, a virus can be attenuated by removal or disruption of viral sequences required for causing disease, while leaving intact those sequences encoding antigens recognized by the immune system. Attenuated viruses may or may not be capable of replication in host cells. Attenuated viruses that are capable of replication are useful because the virus is amplified in vivo after administration to the subject, thus increasing the amount of immunogen available to stimulate an immune response.

According to the invention, a suitable attenuated viral strain may be obtained or generated and one or more of the AGG sequences in the attenuated viral strain mutated to a non-AGG sequence. Several attenuated live viral vaccines have been shown to be useful in protecting against lentiviral or viral infection. For example, live attenuated simian immunodeficiency viruses (SIV) have been used to protect primates against challenge with SIV. See, for example, Daniel et al., "Protective effects of a live attenuated SIV vaccine with a deletion in the nef gene" (1992) Science 258, p 1938; Almond et al., "Protection by attenuated simian immunodeficiency virus in macaques against challenge with virus-infected cells" (1995) Lancet 345, p 1342. The methods of attenuation and attenuated viral strains disclosed in these references may be used in conjunction with the invention. Other methods of attenuation have been described by Desrosiers et al. ("Identification of highly attenuated mutants of simian immunodeficiency virus" (1998) J. Virol. 72, p 1431) and Guan et al. ("Construction and in vitro properties of a series of attenuated simian immunodeficiency viruses with all accessory genes deleted" (2001) J. Virol. 75, p 4056). It should be noted that SIV is a commonly used model for HIV, and attenuation methods useful in SIV may also be useful for HIV. Published patent application WO/2001/007637 describes a live attenuated HIV vaccine modified to replicate only in the presence of a tetracycline analogue. Various other live attenuated HIV strains have been developed, for example "delta 4" which is HIV-1 lacking the nef, vpr, vpu, and Nef-responsive element or NRE genes, and "delta kURN" which is based on the delta 4 vaccine strain but has an additional deletion in the gene encoding the NFkB-binding element. There are also several articles describing how live attenuated HIV vaccines may be generated. See for example, Mills et al. "Live attenuated HIV vaccines: a proposal for further research and development." (2000) AIDS Res Hum Retroviruses 16, p 1453. Any such methods for attenuation may be used in accordance with the invention. If the attenuation methods used involve deletions within the viral genome or within viral nucleic acids, these mutations can be made to be large enough to reduce the chance reversion. For example, 20 bases or more can be deleted if such methods are used.

B) Killed Viral Vaccines

In another embodiment, the invention provides "killed" or "inactivated" viral vaccines having one or more AGG sequences mutated. Such vaccines are generally non-functional and thus do not express viral genes or replicate in the vaccinated subject. However, the methods of the invention may be used to facilitate expansion and growth of virus in vitro or ex vivo prior to inactivation of the virus. For example, by mutating one or more AGG motifs in a virus to a non-AGG sequence, the rate of viral expansion may be increased such that larger amounts of the virus can be produced and then inactivated for use as a vaccine.

Any suitable method of inactivation known in the art may be used to inactivate the mutant viruses of the invention, such as chemical, thermal or physical inactivation or inactivation by irradiation with ionizing radiation. For example, Ilyinskii et al. have developed a physical inactivation method for HIV that utilizes gases to rupture/damage the virus structure in a way that renders it non-infective without comprising its tertiary structure and possible immunogenicity (see Ilyinskii et al. "Development of an Inactivated HIV Vaccine" (2001) AIDS Vaccine Sep. 5-8; abstract no. 192). Others have developed a method of inactivating the HIV virus chemically using 0.2% Beta-propiolactone (BPL) while retaining its immunogenicity (see Addawe et al. "Chemically inactivated whole HIV vaccine induces cellular responses in mice" (1996) Int Conf AIDS Jul. 7-12; 11:4; abstract no. Mo.A.100). Whole-inactivated HIV vaccines have also been tested in human trials. For example, the therapeutic vaccine Remune® (also known as "HIV-1 Immunogen", "Salk vaccine", or "AG1661") which is inactivated by a combination of chemical treatment and irradiation, has been studied as an immunotherapy in HIV-infected patients (see, Fernandez-Cruz et al. "5-year evaluation of a therapeutic vaccine (HIV-1 immunogen) administered with antiretrovirals in patients with HIV chronic infection: induction of long-lasting HIV-specific cellular immunity that impact on viral load" (2003) Second International AIDS Society Conference on HIV Pathogenesis and Treatment, Paris, abstract 486). The methods of the invention can be used in conjunction with any of the above inactivation methods, or other viral inactivation methods known in the art.

C) Viral Vector Vaccines

The lentiviral or viral nucleic acid sequences of the invention mutated to change one or more AGG sequences to a non-AGG sequence may also be incorporated into a viral vector suitable for administration to a subject. The lentiviral or viral nucleic acid may encode any lentiviral or viral protein, including, but not limited to GAG, p17MA, p24CA, p7 and p6, GAG-POL, RT, RNAase H, PR, IN, Gp160, Gp120 ENV, Gp41, Tat, Rev, Vpu, Vif, Vpr and Nef, and fragments, variants, homologues and derivatives thereof. Examples of suitable viral vectors include, but are not limited to, vaccinia viruses (such as Modified Vaccinia Virus Ankara or "MVA", the highly attenuated strain of vaccinia used in smallpox vaccines), retroviruses, poxviruses (including canarypox, vaccinia, and fowlpox) adenoviruses and adeno-associated viruses. These viral vectors may be altered compared to their natural viral counterparts, for example they may be attenuated and/or non-replicative.

One of skill in the art can readily select a suitable viral vector and insert the mutant nucleic acids of the invention into such a vector. The mutant nucleic acid should be under the control of a suitable promoter for directing expression of the lentiviral or viral protein in vaccinated subjects. A promoter that is already present in the viral vector may be used. Alternatively, an exogenous promoter may be used. Examples of suitable promoters include, but are not limited to, the cytomegalovirus (CMV) promoter, the rous sarcoma virus (RSV) promoter, the HIV long terminal repeat (HIV-LTR), the HTLV-1 LTR (HTLV-LTR) and the herpes simplex virus (HSV) thymidine kinase promoter.

Techniques that can be used to insert the nucleic acid sequences of the invention into the viral expression vectors are well known to those of skill in the art. See for example Sambrook et al. (2001) Molecular Cloning: A Laboratory Manual, 3rd Ed., Cold Spring Harbor Laboratory, Cold Spring Harbor, N.Y. ("Sambrook").

The methods of the invention may also be used in conjunction with, or as an improvement to any type of viral vector vaccine known in the art. Examples of HIV viral vector vaccines that are currently in development include Merck's non-replicating adenoviral vector containing HIV Glade B GAG-POL Nef, Sanofi Pasteur's canarypox vector containing Glade B Env, GAG, Pro, RT, and Nef, and Therion's MVA vector containing Glade B Env and GAG. Details of these and other HIV vaccines currently in development are provided by the HIV Vaccine Trials Network at www.hvtn.org. The methods of the invention could be used to improve the efficacy of viral vector vaccines such as these by mutating inhibitory AGG motifs within the lentiviral or viral nucleic acid components to non-AGG sequences, leading in turn to improved expression of the lentiviral or viral proteins in the vaccinated subjects.

DNA Vaccines

The invention also encompasses DNA vaccines suitable for administration to subjects. A lentiviral or viral nucleic acid to change one or more AGG sequences to a non-AGG sequence encoding any lentiviral or viral protein, or portion, fragment, derivative or homologue thereof, may be inserted into a DNA plasmid or expression vector in order to make a DNA vaccine according to the invention. For example, in one embodiment, the DNA vaccine comprises a plasmid containing one or more lentiviral or viral nucleic acids to change one or more AGG sequences to a non-AGG sequence encoding proteins selected from the group consisting of GAG, p17MA, p24CA, p7 and p6, GAG-POL, RT, RNAase H, PR, IN, Gp160, Gp120 ENV, Gp41, Tat, Rev, Vpu, Vif, Vpr and Nef, and fragments, variants, homologues and derivatives thereof.

One of skill in the art can readily select a suitable DNA plasmid or expression vector and insert the mutant nucleic acids of the invention into such a plasmid or expression vector. The nucleic acid encoding the lentiviral or viral protein should be under the control of a suitable promoter for directing expression of the nucleic acid to change one or more AGG sequences to a non-AGG sequence in the vaccinated subjects. A promoter that is already present in the expression vector may be used. Alternatively, an exogenous promoter may be used. Examples of suitable promoters include, but are not limited to, the cytomegalovirus (CMV) promoter, the rous sarcoma virus (RSV) promoter, the HIV long terminal repeat (HIV-LTR), the HTLV-1 LTR (HTLV-LTR) and the herpes simplex virus (HSV) thymidine kinase promoter.

Techniques that can be used to insert the nucleic acid sequences of the invention into DNA plasmids and expression vectors are well known to those of skill in the art. For example, standard recombinant DNA techniques that may be used are described in Sambrook.

The methods of the invention may also be used in conjunction with, or as an improvement to, any type of lentiviral or viral DNA vaccine known in the art. Examples of DNA vaccines that are currently in development include an NIH DNA plasmid containing Glade B Gag, Pol, Nef, and Glade A, B, and C, Env, Chiron's DNA plasmid containing Glade B Gag and Env, and GENEVAX which is a DNA plasmid containing Glade B Gag. Details of these and other HIV vaccines currently in development are provided by the HIV Vaccine Trials Network (HVTN) at www.hvtn.org. The methods of the invention could be used to improve the efficacy of vaccines such as these by mutating inhibitory AGG motifs within the lentiviral or viral nucleic acid components to non-AGG sequences, leading in turn, to improved expression of the lentiviral or viral proteins in the vaccinated subjects.

Protein Vaccines

The invention also encompasses proteinaceous vaccines. Any lentiviral or viral protein, or fragment, derivative, variant or homologue thereof, may be used to make a proteinaceous vaccine according to the invention. For example, in one embodiment, the lentiviral or viral nucleic acid selected to be modified by the methods of the invention is selected from the group consisting nucleic acids encoding GAG, p17MA, p24CA, p7 and p6, GAG-POL, RT, RNAase H, PR, IN, Gp160, Gp120 ENV, Gp41, Tat, Rev, Vpu, Vif, Vpr and Nef, and fragments, variants, homologues and derivatives thereof. The advantage of using the methods of the invention to produce such vaccines, is that by mutating one or more AGG motifs to a non-AGG sequence, the amount of protein produced and/or the rate of protein production may be substantially increased.

In one embodiment, a lentiviral or viral nucleic acid modified by the methods of the invention is incorporated into a suitable expression vector to allow for expression of the protein in a suitable expression system. Examples of suitable expression systems include, but are not limited to, cultured mammalian, insect, bacterial, or yeast cells. The lentiviral or viral proteins or peptides may then be expressed in the cells and purified. The purified proteins can then be incorporated into compositions suitable for administration to subjects. Methods and techniques for expression and purification of recombinant proteins are well known in the art, and any such suitable methods may be used.

Any plasmid or expression vector may be used provided that it contains a promoter to direct expression of the lentiviral or viral protein in the desired expression system. For example, if the protein is to be produced in bacterial cells, a promoter capable of directing expression in bacteria should be used, if the protein is to be produced in mammalian cells, a promoter capable of directing expression in mammalian cells should be used, if the protein is to be produced in insect cells, a promoter capable of directing expression in insect cells should be used, if the protein is to be produced in yeast, a promoter capable of directing expression in yeast should be used. In another embodiment, the proteins are expressed in a mammalian expression system from a mammalian promoter. Suitable promoters include, but are not limited to, the cytomegalovirus (CMV) promoter, the rous sarcoma virus (RSV) promoter, the HIV long terminal repeat (HIV-LTR), the HTLV-1 LTR (HTLV-LTR), the herpes simplex virus (HSV) thymidine kinase promoter, and the SV40 virus early promoter. Suitable expression vectors include but are not limited to cosmids, plasmids, and viral vectors such as replication defective retroviruses, adenoviruses, adeno-associated viruses, herpes viruses, vaccinia viruses, attenuated vaccinia viruses, canary pox viruses, lentiviruses and herpes viruses, among others. Commercially available expression vectors which already contain a suitable promoter and a cloning site for addition of exogenous nucleic acids may also be used.

Any suitable expression system may be used, such as bacterial, yeast, insect, or mammalian cellular expression systems. In another embodiment, the lentiviral or viral proteins are expressed in mammalian cells that have been either stably or transiently transfected with the mutant lentiviral or viral nucleic acids of the invention. Examples of suitable mammalian cells that can be used include, but are not limited to, COS, CHO, BHK, HEK293, VERO, HeLa, MDCK, WI38, and NIH 3T3 cells. Primary or secondary cells obtained directly from a mammal, engineered to contain the mutant nucleic acids of the invention may also be used as an expression system.

One of skill in the art can readily select a suitable expression system, promoter and expression vector for use in accordance with the invention. Examples of workable combinations of cell lines and expression vectors are described in Sambrook. Techniques that can be used to insert the nucleic acid sequences of the invention into an expression vector are well known to those of skill in the art. See, for example, Sambrook.

The methods of the invention may also be used in conjunction with, or as an improvement to, any type of proteinaceous vaccine known in the art. Examples of proteinaceous vaccines that are currently in development include Chiron's protein subunit Glade B Env, and GlaxoSmithKline's Glade B Nef-Tat fusion protein and Glade B Env subunit). The methods of the invention could be used to improve the efficacy of production of vaccines such as these by mutating inhibitory AGG motifs within the nucleic acid that encodes the various protein subunits to non-AGG sequences.

The immunogenic compositions of the invention may comprise subunit vaccines. Subunit vaccines include nucleic acid vaccines such as DNA vaccines, which contain nucleic acids that encode one or more viral proteins or subunits, or portions of those proteins or subunits. When using such vaccines, the nucleic acid is administered to the subject, and the immunogenic proteins or peptides encoded by the nucleic acid are expressed in the subject, such that an immune response against the proteins or peptides is generated in the subject. Subunit vaccines may also be proteinaceous vaccines, which contain the viral proteins or subunits themselves, or portions of those proteins or subunits. Subunit vaccines of the invention may encode or contain any of the lentiviral or viral proteins or peptides described herein, or any portions, fragments, derivatives or mutants thereof, that are immunogenic in a subject. One of skill in the art can readily test the immunogenicity of the lentiviral or viral proteins and peptides described herein, and can select suitable proteins or peptides to use in subunit vaccines.

Vaccine Compositions

The vaccine compositions of the invention comprise at least one virus (including attenuated viruses, inactivated viruses, and viral vectors), nucleic acid, or protein, such as those described above. The compositions may also comprise one or more additional components including, but not limited to, pharmaceutically acceptable carriers, buffers, stabilizers, diluents (such as water), preservatives, solubilizers, or immunomodulatory agents. Suitable immunomodulatory agents include, but are not limited to, adjuvants, cytokines, polynucleotides encoding cytokines, and agents that facilitate recognition by the immune system of at least one component of the vaccines of the invention. One of skill in the art can readily select suitable additives for inclusion in the vaccine compositions of the invention.

A carrier for hydrophobic compounds of the invention can be a co-solvent system comprising benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic immunogenic compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein or other active ingredient stabilization may be employed.

The immunogenic compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the active ingredients of the invention may be provided as salts with immunogenically compatible counter ions. Such immunogenically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The immunogenic composition of the invention may be in the form of a complex of the protein(s) or other active ingredient of invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the immunogenic composition of the invention.

The immunogenic composition of the invention may be in the form of a liposome in which protein of the invention is combined, in addition to other acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithins, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

Other additives that are useful in vaccine formulations are known and will be apparent to those of skill in the art.

Effective Amounts

An "immunologically effective amount" of the vaccine compositions of the invention should be administered to a subject. As used herein, the term "immunologically effective amount" refers to an amount capable of inducing, or enhancing the induction of, the desired immune response in a subject. The desired response may include, inter alia, inducing an antibody or cell-mediated immune response, or both, reducing viral load, ameliorating the symptoms of infection, delaying the onset of symptoms, reducing the duration of infection, and the like. An immunologically effective amount may also be an amount sufficient to induce protective immunity.

One of skill in the art can readily determine what is an "immunologically effective amount" without undue experimentation. For example, an effective amount can be determined by conventional means, starting with a low dose of and then increasing the dosage while monitoring the immunological effects. Numerous factors can be taken into consideration when determining an optimal amount to administer, including the size, age, and general condition of the subject, the presence of other vaccines or drugs in the subject, the virulence of the particular virus against which the subject is being vaccinated, and the like. The actual dosage can be chosen after consideration of the results from various animal studies.

Routes of Delivery/Administration Regimens

The vaccine compositions of the invention may be administered in a single dose, multiple doses, or using "prime-boost" regimens. When prime-boost regimens are used, the vaccines of the invention may be use as the "priming" agent or the "boosting" agent or both. The compositions may be administered by any suitable route, including, but not limited to, parenteral, intradermal, transdermal, subcutaneous, intramuscular, intravenous, intraperitoneal, intranasal, oral, or intraocular routes, or by a combination of routes. The compositions may also be administered using a "gun" device which fires particles, such as gold particles, onto which compositions of the invention have been coated, into the skin of a subject. The skilled artisan will be able to formulate the vaccine composition according to the delivery route chosen.

Viral Purification

Methods of purification of inactivated virus are known in the art and may include one or more of, for instance gradient centrifugation, ultracentrifugation, continuous-flow ultracentrifugation and chromatography, such as ion exchange chromatography, size exclusion chromatography, and liquid affinity chromatography. Additional method of purification include ultrafiltration and dialfiltration. See J P Gregersen "Herstellung von Virussimpfstoffen aus Zellkulturen" Chapter 4.2 in Pharmazeutische Biotecnology (eds. O. Kayser and R H Mueller) Wissenschaftliche Verlagsgesellschaft, Stuttgart, 2000. See also, O'Neil et al., "Virus Harvesting and Affinity Based Liquid Chromatography. A Method for Virus Concentration and Purification", Biotechnology (1993) 11:173-177; Prior et al., "Process Development for Manufacture of Inactivated HIV-1", Pharmaceutical Technology (1995) 30-52; and Majhdi et al., "Isolation and Characterization of a Coronavirus from Elk Calves with diarrhea" Journal of Clinical Microbiology (1995) 35(11): 2937-2942.

Other examples of purification methods suitable for use in the invention include polyethylene glycol or ammonium sulfate precipitation (see Trepanier et al., "Concentration of human respiratory syncytial virus using ammonium sulfate, polyethylene glycol or hollow fiber ultrafiltration" Journal of Virological Methods (1981) 3(4):201-211; Hagen et al., "Optimization of Poly(ethylene glycol) Precipitation of Hepatitis Virus Used to prepare VAQTA, a Highly Purified Inactivated Vaccine" Biotechnology Progress (1996) 12:406-412; and Carlsson et al., "Purification of Infectious Pancreatic Necrosis Virus by Anion Exchange Chromatography Increases the Specific Infectivity" Journal of Virological Methods (1994) 47:27-36) as well as ultrafiltration and microfiltration (see Pay et al., Developments in Biological Standardization (1985) 60:171-174; Tsurumi et al., "Structure and filtration performances of improved cuprammonium regenerated cellulose hollow fibre (improved BMM hollow fibre) for virus removal" Polymer Journal (1990) 22(12): 1085-1100; and Makino et al., "Concentration of live retrovirus with a regenerated cellulose hollow fibre, BMM", Archives of Virology (1994) 139(1-2):87-96.).

Viruses can be purified using chromatography, such as ion exchange, chromatography. Chromatic purification allows for the production of large volumes of virus containing suspension. The viral product of interest can interact with the chromatic medium by a simple adsorption/desorption mechanism, and large volumes of sample can be processed in a single load. Contaminants which do not have affinity for the adsorbent pass through the column. The virus material can then be eluted in concentrated form.

Anion exchange resins that may be used include DEAE, EMD TMAE. Cation exchange resins may comprise a sulfonic acid-modified surface. Viruses can be purified using ion exchange chromatography comprising a strong anion exchange resin (e.g. EMD TMAE) for the first step and EMD-SO.sub.3 (cation exchange resin) for the second step. A metal-binding affinity chromatography step can optionally be included for further purification. (See, e.g., WO 97/06243).

A resin such as Fractogel™ EMD. Can also be used This synthetic methacrylate based resin has long, linear polymer chains (so-called "tentacles") covalently attached. This "tentacle chemistry" allows for a large amount of sterically accessible ligands for the binding of biomolecules without any steric hindrance. This resin also has improved pressure stability.

Column-based liquid affinity chromatography is another purification method that can be used invention. One example of a resin for use in purification method is Matrex™ Cellufine™ Sulfate (MCS). MCS consists of a rigid spherical (approx. 45-105 .mu.m diameter) cellulose matrix of 3,000 Dalton exclusion limit (its pore structure excludes macromolecules), with a low concentration of sulfate ester functionality on the 6-position of cellulose. As the functional ligand (sulfate ester) is relatively highly dispersed, it presents insufficient cationic charge density to allow for most soluble proteins to adsorb onto the bead surface. Therefore the bulk of the protein found in typical virus pools (cell culture supernatants, e.g. pyrogens and most contaminating proteins, as well as nucleic acids and endotoxins) are washed from the column and a degree of purification of the bound virus is achieved.

The rigid, high-strength beads of MCS tend to resist compression. The pressure/flow characteristics the MCS resin permit high linear flow rates allowing high-speed processing, even in large columns, making it an easily scalable unit operation. In addition a chromatographic purification step with MCS provides increased assurance of safety and product sterility, avoiding excessive product handling and safety concerns. As endotoxins do not bind to it, the MCS purification step allows a rapid and contaminant free depyrogenation. Gentle binding and elution conditions provide high capacity and product yield. The MCS resin therefore represents a simple, rapid, effective, and cost-saving means for concentration, purification and depyrogenation. In addition, MCS resins can be reused repeatedly.

Inactivated viruses may be further purified by gradient centrifugation, or density gradient centrifugation. For commercial scale operation a continuous flow sucrose gradient centrifugation would be an option. This method is widely used to purify antiviral vaccines and is known to one skilled in the art (See J P Gregersen "Herstellung von Virussimpfstoffen aus Zellkulturen" Chapter 4.2 in Pharmazeutische Biotechnology (eds. O. Kayser and R H Mueller) Wissenschaftliche Verlagsgesellschaft, Stuttgart, 2000.)

Additional purification methods which may be used to purify viruses of the invention include the use of a nucleic acid degrading agent, a nucleic acid degrading enzyme, such as a nuclease having DNase and RNase activity, or an endonuclease, such as from *Serratia marcescens*, commercially available as Benzonase™ membrane adsorbers with anionic functional groups (e.g. Sartobind™) or additional chromatographic steps with anionic functional groups (e.g. DEAE or TMAE). An ultrafiltration/dialfiltration and final sterile filtration step could also be added to the purification method.

The purified viral preparation of the invention is substantially free of contaminating proteins derived from the cells or cell culture and can comprises less than about 1000, 500, 250, 150, 100, or 50 pg cellular nucleic acid/.mu.g virus antigen, and less than about 1000, 500, 250, 150, 100, or 50 pg cellular nucleic acid/dose. The purified viral preparation can also comprises less than about 20 pg or less than about 10 pg. Methods of measuring host cell nucleic acid levels in a viral sample are known in the art. Standardized methods approved or recommended by regulatory authorities such as the WHO or the FDA can be used.

Other Embodiments of the Invention

In other embodiments, the invention is directed to methods for identifying agents that inhibit or stimulate production of viral RNA, production of viral protein or production of viral particles, or that inhibit or stimulate viral latency. In another embodiment, the method comprises providing a control cell containing at least one viral nucleic acid sequence containing at least one AGG motif, and a test cell containing at least one viral nucleic acid sequence containing at least one AGG motif that has been mutated to a non-AGG sequence, contacting the test cell and the control cell with one or more agents, and identifying at least one agent that inhibits or stimulates production of viral RNA, production of virus protein or production of virus particles, or that inhibits or stimulates viral latency, in the test cell as compared to the control cell.

In other embodiments, the invention is directed to methods for identifying agents that inhibit or stimulate production of lentiviral RNA, production of lentiviral protein or production of lentiviral particles, or that inhibit or stimulate lentiviral latency. In another embodiment, the method comprises providing a control cell containing at least one lentiviral or viral nucleic acid sequence containing at least one AGG motif, and a test cell containing at least one lentiviral or viral nucleic acid sequence containing at least one AGG motif that has been mutated to a non-AGG sequence, contacting the test cell and the control cell with one or more agents, and identifying at least one agent that inhibits or stimulates production of lentiviral or viral RNA, production of lentivirus or virus protein or production of lentivirus or virus particles, or that inhibits or stimulates lentiviral or viral latency, in the test cell as compared to the control cell.

In some embodiments, the agents inhibit or stimulate production of HIV RNA, production of HIV protein or production of HIV particles, or inhibit or stimulate HIV latency. For example, entire "libraries" of agents can be screened in this way using high throughput screening methods. One of skill in the art could readily design a high throughput screening method to identify agents that inhibit or stimulate production of lentiviral or viral RNA, production of lentivirus or virus protein or production of lentivirus or virus particles, or that inhibit or stimulate viral latency. Methods for growing cells in multiwell plates are well known, and methods for administering different agents from a library of agents to different wells of multiwell plates are known. Several methods could be used to determine the effects of the library agents on production of lentiviral or viral RNA, production of lentiviral or viral protein or production of lentiviral or viral particles, or on lentiviral or viral latency. For example, the cells used for the high throughput screening could be engineered to encode one or more fusion proteins, such as a fusion between a lentiviral or viral protein and a fluorescent protein such as green fluorescent protein (GFP). In this way, production of lentiviral or viral proteins could be monitored by fluorescent detection methods, which would enable agents that stimulate or inhibit production of the lentiviral or viral protein to be detected.

In another embodiment, the invention is directed to methods for identifying AGG motif binding agents. In one embodiment, the method comprises providing a control nucleic acid containing at least one AGG motif and a test nucleic acid containing at least one AGG motif that has been mutated to a non-AGG sequence, contacting the test nucleic acid and the control nucleic with one or more agents, and identifying at least one agent that binds to the control nucleic acid but does not bind the test nucleic acid, or that binds to the control nucleic acid with a higher affinity than it binds to the test nucleic acid. In another embodiment, the method comprises providing a test nucleic acid containing multiple repeating AGG motifs and a control nucleic acid containing a random assortment and order of nucleotides, contacting the test nucleic acid and the control nucleic with one or more agents, and identifying at least one agent that binds to the test nucleic acid but does not bind the test control acid, or that binds to the test nucleic acid with a higher affinity than it binds to the control nucleic acid. There are multiple ways in which agents that bind to these constructs could be detected. For example, in one embodiment, the above test and control nucleic acids could be provided on a column or one some other suitable solid substrate, and test samples (such as cell lysates or libraries of test agents) could be passed over these substrates. Agents that bind to the test and/or control substrates could be eluted and analyzed. In other embodiments, yeast one-hybrid methods could be used to identify agents that bind to AGG motifs. In further embodiments, electrophoretic mobility shift assays (EMSAs) could be performed to identify agents that bind to AGG motifs. Other methods suitable for identifying nucleotide binding agents are known in the art, and any such method could be used to identify agents that bind to AGG motifs. The invention also encompasses AGG motif binding agents, such as those identified using the methods of the invention.

In yet another embodiment, the invention is directed to agents that inhibit or stimulate binding of an AGG-binding agent to a nucleic acid containing at least one AGG motif, and to methods for identifying such agents as described above.

These and other embodiments of the invention are further described in the following non-limiting examples.

EXAMPLES

Example 1

Identification of AGG Motif in HIV-1 Genome

Because the genetic code is degenerate, nucleotide sequences can differ from each other at the nucleotide level but encode the same protein or peptide. However, in nature there is often selective pressure for particular codon usage and AT/GC content. There is also selective pressure for the frequency and order of amino acids in the proteins encoded by the nucleotide sequences. A method that normalizes for each of these selection pressures, and then calculates the average frequency of sequence motifs (for example, sequence motifs of 2-8 nucleotides in length) expected in a genome and compares this to the actual frequency of these motifs in that genome, was used to look for sequence motifs that are over- and under-represented in the HIV-1 genome as compared to the human genome. This method is described in co-pending provisional patent application No. 60/808,420, and Robins et al. (Journal of Bacteriology, (2005) Vol. 187, p. 8370-74, the contents of which are hereby incorporated by reference.

Based on the biology of the HIV agent described above, the HIV genome is likely to contain one or more INS motifs. We predicted that these motifs would not be present in host (i.e. human) genes that have a comparable A-rich content (the HIV genome has a high A-content). 4,000 human genes having A-contents comparable to HIV were identified and studied using the methods described above. A sequence motif, AGG, was identified that was under-represented in these human genes as compared to the expected frequency. The same AGG motif was found to be over-represented in both the gag gene and the pol gene of the HIV-1 genome. Of 48 AGG oligonucleotide sequences present in the gag gene (as shown in FIG. 1), over two thirds were not in the reading frame that encodes an amino acids, suggesting that these sequences were not conserved due to selection at the amino acid/protein level. While third codon position changes are common in different HIV isolates, the AGG motif was also found to be particularly conserved even in the third position of codons. Furthermore, the AGG motif was also found to be over-represented in over 400 different HIV-1 strains analyzed (all were found to contain between 44-48 copies of the AGG motif). These results suggest that the AGG motif may have been selected against in the human genome (i.e. in the HIV host), while being retained and/or enriched in the HIV genome. Taken together, these results suggest that the AGG motif may be an INS sequence.

Example 2

Identification of the AGG Motif in Other Lentiviruses

The presence of the AGG motif was investigated in a wide variety of Lentiviruses, including HIV-2, several strains of simian immunodeficiency virus (SIV), feline immunodeficiency virus (FIV) and equine infectious anemia virus (EIAV). All of these viruses were found to have the expected or a higher than expected frequency of the AGG motif. However, it was found that the human T-cell leukaemia virus (HTLV-1) and the human retrotransposon LINE-1 did not have the expected or higher than expected frequency of the AGG motif.

Example 3

Method for Identification of Other INS Sequences

It is possible that the HIV genome contains additional INS sequences in addition to the AGG motif. It is also possible that the AGG motif forms part of a larger INS sequence or sequences. The methods described above for identification of the AGG motif can be applied to discover further INS sequences in the HIV genome, or indeed in the genome of any other virus, such as other lentiviruses, or other retroviruses.

Example 4

Function of the AGG Motif

The role of the AGG motifs will be tested by mutating one or more of the motifs without changing the coding for amino acids. For example, plasmids containing wild type or mutant HIV-1 gag sequences, each regulated by the HIV LTR, will be transfected (transiently or stably) into the same cell type and the steady state levels of gag mRNAs that are produced will be measured, for example using real time PCR. This experiment will test whether the AGG sequences in the gag gene affect the rate of transcription, the transport of this mRNA into the cytoplasm or the half-life of the mRNA. This same experiment will be repeated with a construct having one or more AGG sequences mutated in both the gag and pol regions.

In order to look at the effects of the AGG motif at the protein level, constructs containing the coding sequences for GAG-POL and green fluorescent protein (GFP) will be used. Cells producing GAG-POL-GFP can then be detected using standard fluorescence detection methods, such as fluorescence microscopy. Flow cytometry and fluorescence-activated cell sorting can also be used. Cells will be transfected with nucleic acid encoding either wild type GAG-POL-GFP, or mutant GAG-POL-GFP (i.e. a construct having one or more AGG motifs mutated to a non-AGG motif). It is expected that there will be a much higher level of GFP detected in cells transfected with the mutant sequences.

If this experiment gives the expected results this will prove (1) that the AGG motifs are INS sequences, and (2) that the AGG INS sequences can act to lower the steady state level of HIV mRNA in cells.

The TAT and REV dependence of these constructs will also be tested. It is expected that cells transfected with the AGG mutant constructs will make high levels of GAG-POL RNA (perhaps 70-130 fold higher than the wild-type constructs) even in the absence of TAT and REV. Co-transfecting the cells with TAT and/or REV expression constructs, or including TAT and REV coding sequences in the GAG-POL constructs, is expected to increase the levels of GAG-POL RNA even further.

Example 5

Vaccines

To date, there is no commercially available vaccine capable of conferring immunity against HIV challenge. There are many reasons why it has not been possible to generate such a vaccine. One factor that may have contributed to the difficulty in producing a vaccine could be the ability of HIV to remain intracellular for extended periods of time. Intracellular virus is protected from antibody-mediated (but not CD-8 T-cell-mediated) immunity. The HIV virus is able to remain hidden intracellularly for long periods because of its slow rate of production inside cells, its ability to remain latent inside cells, and its ability to spread from cell to cell by cell fusion provides.

These properties of the HIV virus may adversely affect the ability to generate an effective vaccine on multiple levels. On one level, vaccines based on the HIV virus, such as inactivated or attenuated HIV vaccines, may enter and remain in host cells for extended periods of time, as do wild type HIV viruses. Thus, because of the slow life cycle of the virus and the limited amount of time during which the viruses are exposed extracellularly, the immune system is not able to generate an immune response strong enough to provide protective immunity against subsequent challenge with HIV. On another level, DNA may express very low levels of HIV-encoded antigens due to the presence of INS sequences, such as AGG motifs, in the nucleic acid constructs used. Generally, the more antigen that is produced, the greater the immune response will be. Thus, if low levels of HIV-antigens are produced, the immune response generated against those antigens will also be low.

It may be possible to overcome these problems, and thus generate more effective vaccines, by mutating one or more AGG motifs within the viral nucleic acids used in, or used to produce, vaccines. For example, an attenuated HIV vaccine could be produced which in addition to being altered so as to reduce its ability to cause disease, is also mutated to disrupt on or more AGG motifs.

To test the above approaches, attenuated HIV viruses having mutated AGG motifs will be generated. The ability of these mutated viruses to infect host cells, express the encoded HIV proteins, and produce new virus particles will be studied in vitro using cell culture systems. Also, the ability of these mutated viruses to generate an immune response in a host in vivo, will be tested using suitable animal models of HIV infection.

In addition, the same approach will be tested using the SIV virus and the FIV virus. Attenuated FIV and SIV viruses having mutated AGG motifs will be generated. The ability of these mutated viruses to infect host cells will be studied in vitro using cell culture systems. Also, the ability of theses mutated viruses to generate an immune response will be tested in vivo in hosts susceptible to SIV and/or HIV infection. These SIV and FIV experiments will provide useful models for HIV vaccines/HIV infection. Additionally, the generation and testing of vaccines against SIV in simian species, and the generation and testing of vaccines against FIV in feline species, are useful in of themselves. Immunological compositions capable of providing protection against SIV challenge in simian species and/or immunological compositions capable of providing protection against FIV challenge in feline species, are within the scope of the invention.

Example 6

Model for HIV Latency and Role of AGG Motif in Latency

In experiments similar to those described above, wild type and mutant gag-pol constructs will be stably transfected into cells. It is expected that cell lines having integrated copies of the wild type AGG will produce low levels of the GAG and POL RNAs and proteins because of the activity of the AGG sequences. It is also expected that some of the clones will not produce any GAG-POL mRNA or protein due to the phenomenon of stochastic phenotypic switching which is believed to be involved in latency. These clones will provide a cell culture model of latency.

In order to distinguish those clones expressing low levels of GAG-POL from those expressing no GAG-POL, a GAG-POL-GFP expression construct may be used. Thus cells expressing GAG-POL-GFP can be detected by fluorescence detection methods, and cell sorting (such as fluorescence-activated cell sorting or FACS) can be used to separate the two, i.e. those expressing and those not expressing GAG-POL-GFP. It will also be possible to test these clones to confirm that they do in fact contain an integrated copy of the nucleic acid encoding the GAG-POL-GFP protein(s)

According to the stochastic phenotypic switching model of HIV latency, we expect that a percentage of the non-expressing clones will at some point turn on the expression of the GAG-POL-GFP. The frequency/rate at which the GAG-POL genes are switched on, and the environmental variables that affect the switch can then be measured. Such a model will be useful for identifying agents (such as protease inhibitors, reverse transcriptase inhibitors, DNA damaging agents, and other agents) that reverse HIV latency and thus make the virus more responsive to treatment.

This model can also be used to investigate the effect of the AGG motif on latency. It is expected that, in the absence of REV and TAT, the AGG sequences may act to reduce steady state levels of HIV RNA. It is also possible that the AGG motif may be capable of eliminating production of HIV RNA altogether as occurs in latency. Indeed, it is possible that the AGG motif is responsible for, or an important factor in, HIV latency.

Example 7

AGG Binding Proteins and Agents

It has been proposed that INS sequences may act by binding a cellular protein, which in turn acts to produce chromatin that is inactive for transcription (see Schneider et al.). In this study, nine cellular genes, out of 4,000 genes screened, that have AGG frequencies as high as HIV were identified. It is therefore possible that there is a cellular AGG binding protein present in human cells. In order to determine if such a protein exists, and if so isolate the protein, T-cell extracts will be passed over AGG oligonucleotide columns with washes of competitor human DNA. If such a protein is identified, the amino acid sequence of the protein will be determined, and the gene encoding the protein will be identified.

If identified, such an AGG-binding protein, or agents that mimic the effects of the protein (i.e. by binding to the AGG), could be useful for inducing viral latency. This may be desirable in some circumstances—if latency can be induced by treatment with an agent, it could be possible to minimize or eliminate altogether any the consequences of HIV infection in an infected host. Such a protein or agent would also be expected to have only minimal side effects on the host, as the great majority of host genes have 100 fold lower AGG frequencies than those of HIV.

Furthermore, if such an AGG-binding protein is identified, it may be possible to screen for agents that block, or reduce the affinity of the binding of the protein to the AGG, or otherwise disrupt the activity of the AGG-binding. Such agents could be useful for reversing latency ing turnover of the HIV virus. Such effects may be desirable in certain situations, for example to increase the ability of other drug and/or vaccines to eradicate an HIV infection.

The effects of AGG-binding proteins, agents that mimic the effects of AGG-binding proteins, and agents that block, reduce the affinity of, or otherwise disrupt the activity of AGG-binding proteins, can be tested using the models described herein, and can also be tested in animal models for HIV, such as SIV and/or FIV.

Example 8

Identification of Multiple Nucleotide Motifs in a Systematic Comparison of the HIV-1 Genome and the Human Genome In this example, multiple nucleotide motifs suspected to play a causative role in nuclear confinement are identified in a systematic comparison of the HIV-1 genome and the human genome. The short motif, AGG, is identified, which has the maximal differential representation between the coding genes in the human genome and the HIV-1 genome. This identification was made through the use of the methods of the invention. The method identifies dozens of motifs that exhibit substantial differences in representation between the HIV-1 genome and the human coding genes. The results presented in this example focus on a single motif in order to isolate its contribution to expression level in a controlled experiment. A codon optimized version of Gag is modified, making synonymous changes to reduce the number of occurrences of AGG. Two plasmids are created, one with the original codon optimized (CO) sequence of Gag and the other with the motif optimized (MO) sequence with AGG significantly reduced. The constructs are transfected into a human epithelial cell line (293 cells) and expression of Gag is shown to be 70% higher for the MO sequence. The two sequences of Gag are also made into injectable mouse vaccines to test for differential antibody response between the two constructs. The mice with the MO version of the vaccine have a 4.5 fold greater anti-Gag antibody response after 4 weeks. With a DNA boost at four weeks and a second readout at six weeks, the gap continues to widen between the MO and CO vaccines.

A method of the invention (the Robins-Krasnitz method described above) finds short nucleotide motifs in coding regions of the human genome that are independent of amino acid order and codon usage. Codon usage is defined to mean the total fraction of each codon used in a given gene. The result of the Robins-Krasnitz method is a set of exact nucleotide motifs of length 2-7 bases which are under and over represented in the coding regions of the human genome. It is these motifs which are compared to the HIV genome. The first step in the Robins-Krasnitz method is the creation of a background sequence to compare with the human genome. This background is a completely randomized version of the coding sequences from the human genome subject to the constraints of amino acid order and codon usage in each gene. A Monte Carlo program that randomly permutes the codons for each amino acid within each gene can be designed. Table 1 is an illustrative example.

TABLE 1

Example of shuffling procedure

M $L_1$ $L_2$ $H_1$ $L_3$ $H_2$ $L_4$ $H_3$ ST
ATG CTA CTG CAT TTA CAT CTG CTT TAG

The procedure to get the maximal entropy distribution (MED) involves a set of randomized iterations. The triplets of nucleotides coding for each amino acid are permuted randomly among themselves. This is an illustrative example of a mock short protein with eight amino acids. The shuffling procedure randomly permutes $L_1$, $L_2$, $L_3$, and $L_4$ and separately permutes $H_1$, $H_2$, and $H_3$. Each iteration produces a new sequence. For this example, there are 12 different combinations for the leucines and three combinations for the histidines giving 36 unique sequences. They are weighted in the shuffling procedure so that the MED is attained in the limit of a large number of iterations.

The shuffling procedure described above gives a set of randomized sequences. A probability distribution is extracted form these sequences. As long as the number of occurrences of each motif found in the total set of sequences is reasonably large, a probability distribution can be formed by estimating the probability of a given motif by its fraction in the set of all motifs.

After the shuffling procedure, two distributions are defined, the real distribution found from the actual sequence and the Maximal Entropy Distribution (MED) which is used as the surrogate for the background. An information theory standard is used as a method for choosing under and over represented motifs. The motif that contributes the most bits of information to the difference between the real distribution and the MED is the first motif chosen. Using information theory has the nice feature of putting all results in the same units, number of bits. This allows a comparison of motifs of different lengths and motifs that are either over or under represented. The formula employed to compute the motif contributing the most bits of information between the two distributions is the Kullback-Leibler distance or the Relative Entropy. The Relative Entropy contribution for each motif is computed and the largest value is selected.

Once the most under- or over-represented motif in the sequence is identified, the motif which is the next most under- or over-represented is selected. However, once cannot simply take the motif which has the next largest Relative Entropy. This is because the motifs are overlapping, so under or over representation of a given motif affects the distribution of all the other motifs. The example of CpG illustrates this point. In the human genome, the dinucleotide motif CG will have the largest Relative Entropy. However, all eight trimers which contain CG as a subset fall within the top 50 highest Relative Entropy motifs. This is simply an artifact of the selection against CG. It is required that the contribution of CG from the MED be removed before recalculating the Relative Entropy to find the next motif. If the motif is called w, all motifs that contain w are rescaled by the same amount such that the rescaled MED had the same distribution for was the real distribution. This forces the Relative Entropy of w to zero and, at the same time, removes the contribution of w from all other motifs. This choice of rescaling monotonically decreases the overall Relative Entropy between the distributions.

The procedure is reiterated, so that the contribution of one motif at a time is removed from the Relative Entropy through rescaling of the MED. Then, the next motif is chosen. As iteration of the procedure continues, and additional motifs are found, until the motif with the largest remaining Relative Entropy is not statistically significant, as determined by comparing shuffled genomes.

Beginning with the set of the 100 most under- and over-represented motifs in the human genome, the methods presented herein identify the motif having the largest density difference between the HIV genome and the human genome, after total "A" content is taken into consideration. The motifs are restricted to the set of human genes with "A" content within 1% of the average HIV "A" content. The ratios of the densities in the HIV genome are then divided by densities in the human coding regions. If the human density is greater than that of HIV, the quantity is replaced by its reciprocal. The motif with the largest ratio of densities is the prediction for a causative signal for nuclear isolation of HIV mRNAs.

The AGG triplet, which is extremely under-represented in the coding region of the human genome, is found with high frequency in HIV considering the nucleotide bias. It is an object of this invention that recoding the ORFs of HIV by reducing the frequency of the motif AGG will increase protein expression.

For this study, the experimental tests focused on the Gag gene. The codon optimized sequence of Gag, referred to as Adarc-Gag, is recoded by systematically removing all AGGs such that the amino acid sequence is not modified and very rare codons are not introduced. The result is RK-Gag.

The first step is to determine if RK-Gag has increased expression as compared to the codon optimized verion, Adarc-Gag. Since the modifications in RK-Gag undo part of the codon optimization, the protein expression levels should be expected to decrease unless the motif AGG is significantly inhibiting mRNA processing or transport. To compare expression levels, human 293 cells were transfected in vitro with one of the two different versions of Gag. Measuring the protein levels, RK-Gag was 70% higher than the codon optimized Adarc-Gag (FIG. 2).

To test the effect of the almost two-fold gain in expression on immune response, DNA vaccines were created from each of the sequences. These DNA vaccines were injected into the hind leg muscle of Balb/C mice and then given a booster shot after four weeks. Anti-Gag antibody titers were measured by anti-P24 ELISA at the four week and six week time points (see method for details). The results are found in FIG. 3. The 70% increase in expression in vitro translated into more than a five fold difference in humoral immune response in a mouse model.

Recoding the Gag gene to reduce the occurrences of a single triplet substantially improved immune response to an HIV DNA vaccine in a mouse model. This short motif is rarer in the human coding sequence than mouse, so the results would be expected to be even more dramatic in humans. A set of steps may be required to move in the direction a clinically viable vaccine including recoding the ENV ORF as well and testing its ability to induce an immune response. Another step may be looking for neutralizing antibody responses in primates. The intent of this work is to provide evidence that recoding the HIV ORFs can greatly improve expression and immune response over present codon optimization schemes. Moreover, the application of a method of the invention is an effective means of generating a set of motifs that should be incorporated into the recoding procedure. Systematic inclusion of other motifs determined by the methods of the invention has the potential to improve upon the large gains displayed in this example.

We claim:

1. A method for increasing production of a lentiviral protein in a host cell or in a cell-free translation system, the method comprising:
   (a) providing a first lentiviral nucleic acid sequence comprising a plurality of AGG sequences, and encoding a lentiviral protein, wherein
      (i) the first lentiviral nucleic acid sequence is a wild type lentiviral nucleic acid sequence or a codon optimized lentiviral nucleic acid sequence,
   (b) altering the sequence of the first lentiviral nucleic acid sequence to replace one or more AGG sequences with a non-AGG sequence to generate an altered lentiviral nucleic acid sequence, wherein
      (i) the altering of step (b) does not change the amino acid sequence of the lentiviral protein or introduce rare codons,
      (ii) wherein the altered lentiviral nucleic acid sequence of step (b) has a reduced number of AGG sequences compared to the first lentiviral nucleic acid sequence of step (a), and
      (iii) wherein the altered lentiviral nucleic acid sequence of step (b) is expressed more in a host cell or in a cell-free translation system as compared to the first lentiviral sequence.

2. The method of claim 1, wherein the altering comprises introducing at least one nucleic acid substitution in the first lentiviral nucleic acid sequence.

3. The method of claim 1, wherein the altering comprises introducing at least one nucleic acid deletion in the first lentiviral nucleic acid sequence.

4. The method of claim 1, wherein the altering comprises introducing at least one nucleic acid addition in the first lentiviral nucleic acid sequence.

5. The method of claim 1, wherein the altering comprises mutating at least one AGG sequence spanning at least two codons of the first lentiviral nucleic acid sequence.

6. A method for increasing production of a lentiviral protein in a host cell or in a cell-free translation system, the method comprising:
   (a) providing a first lentiviral nucleic acid sequence encoding a lentiviral protein, wherein the first lentiviral nucleic acid sequence is a wild type lentiviral nucleic acid sequence or a codon optimized lentiviral nucleic acid sequence,
   (b) altering the first lentiviral nucleic acid sequence encoding the lentiviral viral protein so as to reduce the number of AGG sequences in the lentiviral nucleotide sequence encoding the lentiviral viral protein, and wherein the altering of step (b) does not change the amino acid sequence of the lentiviral protein or introduce rare codons, and wherein the altered lentiviral nucleic acid sequence of step (b) is expressed more in a host cell or in a cell-free translation system as compared to the first lentiviral sequence.

7. A method for increasing production of a lentiviral protein in a host cell or in a cell-free translation system, the method comprising:
   (a) providing a first lentiviral nucleic acid sequence encoding a lentiviral protein, wherein the first lentiviral nucleic acid sequence is a wild type lentiviral nucleic acid sequence or a codon optimized lentiviral nucleic acid sequence,
   (b) altering the first lentiviral nucleic acid sequence encoding the lentiviral protein to reduce the number of AGG sequences in the first nucleic acid sequence to generate an optimized sequence, wherein the optimized sequence comprises fewer AGG sequences than the first lentiviral nucleic acid sequence, and wherein the altering does not change the amino acid sequence of the lentiviral protein or introduce rare codons, and wherein the optimized sequence is expressed more in a host cell or in a cell-free translation system as compared to the first lentiviral sequence.

8. The method of claim 6 or 7, wherein the altering comprises introducing at least one nucleic acid substitution in the first lentiviral nucleic acid sequence.

9. The method of claim 6 or 7, wherein the altering comprises introducing at least one nucleic acid deletion in the first lentiviral nucleic acid sequence.

10. The method of claim 6 or 7, wherein the altering comprises introducing at least one nucleic acid addition in the lentiviral first nucleic acid sequence.

11. The method of claim 6 or 7, wherein the altering comprises mutating at least one AGG sequence spanning at least two codons of the first lentiviral nucleic acid sequence.

12. The method of any of claim 1, 6 or 7, wherein the lentiviral protein is a retroviral protein.

13. The method of any of claim 1, 6 or 7, wherein the lentiviral protein is an HIV protein.

\* \* \* \* \*

```
                        SEQUENCE LISTING

<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Leu Leu His Leu His Leu His
  1               5

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atgctactgc atttacatct gctttag                                        27

<210> SEQ ID NO 3
<211> LENGTH: 1503
<212> TYPE: DNA
<213> ORGANISM: Human immunodeficiency virus
<220> FEATURE:
<221> NAME/KEY: CDS
<222> LOCATION: (1)..(1500)

<400> SEQUENCE: 3 atg ggt gcg aga gcg tcg gta tta agc ggg gga gaa tta gat aaa tgg      48
Met Gly Ala Arg Ala Ser Val Leu Ser Gly Gly Glu Leu Asp Lys Trp
 1               5                  10                  15
```

-continued

| | | |
|---|---|---|
| gaa aaa att cgg tta agg cca ggg gga aag aaa caa tat aaa cta aaa<br>Glu Lys Ile Arg Leu Arg Pro Gly Gly Lys Lys Gln Tyr Lys Leu Lys<br>20 25 30 | | 96 |
| cat ata gta tgg gca agc agg gag cta gaa cga ttc gca gtt aat cct<br>His Ile Val Trp Ala Ser Arg Glu Leu Glu Arg Phe Ala Val Asn Pro<br>35 40 45 | | 144 |
| ggc ctt tta gag aca tca gaa ggc tgt aga caa ata ctg gga cag cta<br>Gly Leu Leu Glu Thr Ser Glu Gly Cys Arg Gln Ile Leu Gly Gln Leu<br>50 55 60 | | 192 |
| caa cca tcc ctt cag aca gga tca gaa gaa ctt aga tca tta tat aat<br>Gln Pro Ser Leu Gln Thr Gly Ser Glu Glu Leu Arg Ser Leu Tyr Asn<br>65 70 75 80 | | 240 |
| aca ata gca gtc ctc tat tgt gtg cat caa agg ata gat gta aaa gac<br>Thr Ile Ala Val Leu Tyr Cys Val His Gln Arg Ile Asp Val Lys Asp<br>85 90 95 | | 288 |
| acc aag gaa gcc tta gat aag ata gag gaa gag caa aac aaa agt aag<br>Thr Lys Glu Ala Leu Asp Lys Ile Glu Glu Glu Gln Asn Lys Ser Lys<br>100 105 110 | | 336 |
| aaa aag gca cag caa gca gca gct gac aca gga aac aac agc cag gtc<br>Lys Lys Ala Gln Gln Ala Ala Ala Asp Thr Gly Asn Asn Ser Gln Val<br>115 120 125 | | 384 |
| agc caa aat tac cct ata gtg cag aac ctc cag ggg caa atg gta cat<br>Ser Gln Asn Tyr Pro Ile Val Gln Asn Leu Gln Gly Gln Met Val His<br>130 135 140 | | 432 |
| cag gcc ata tca cct aga act tta aat gca tgg gta aaa gta gta gaa<br>Gln Ala Ile Ser Pro Arg Thr Leu Asn Ala Trp Val Lys Val Val Glu<br>145 150 155 160 | | 480 |
| gag aag gct ttc agc cca gaa gta ata ccc atg ttt tca gca tta tca<br>Glu Lys Ala Phe Ser Pro Glu Val Ile Pro Met Phe Ser Ala Leu Ser<br>165 170 175 | | 528 |
| gaa gga gcc acc cca caa gat tta aat acc atg cta aac aca gtg ggg<br>Glu Gly Ala Thr Pro Gln Asp Leu Asn Thr Met Leu Asn Thr Val Gly<br>180 185 190 | | 576 |
| gga cat caa gca gcc atg caa atg tta aaa gag acc atc aat gag gaa<br>Gly His Gln Ala Ala Met Gln Met Leu Lys Glu Thr Ile Asn Glu Glu<br>195 200 205 | | 624 |
| gct gca gaa tgg gat aga ttg cat cca gtg cat gca ggg cct att gca<br>Ala Ala Glu Trp Asp Arg Leu His Pro Val His Ala Gly Pro Ile Ala<br>210 215 220 | | 672 |
| cca ggc cag atg aga gaa cca agg gga agt gac ata gca gga act act<br>Pro Gly Gln Met Arg Glu Pro Arg Gly Ser Asp Ile Ala Gly Thr Thr<br>225 230 235 240 | | 720 |
| agt acc ctt cag gaa caa ata gga tgg atg aca cat aat cca cct atc<br>Ser Thr Leu Gln Glu Gln Ile Gly Trp Met Thr His Asn Pro Pro Ile<br>245 250 255 | | 768 |
| cca gta gga gaa atc tat aaa aga tgg ata atc ctg gga tta aat aaa<br>Pro Val Gly Glu Ile Tyr Lys Arg Trp Ile Ile Leu Gly Leu Asn Lys<br>260 265 270 | | 816 |
| ata gta aga atg tat agc cct acc agc att ctg gac ata aga caa gga<br>Ile Val Arg Met Tyr Ser Pro Thr Ser Ile Leu Asp Ile Arg Gln Gly<br>275 280 285 | | 864 |
| cca aag gaa ccc ttt aga gac tat gta gac cga ttc tat aaa act cta<br>Pro Lys Glu Pro Phe Arg Asp Tyr Val Asp Arg Phe Tyr Lys Thr Leu<br>290 295 300 | | 912 |
| aga gcc gag caa gct tca caa gag gta aaa aat tgg atg aca gaa acc<br>Arg Ala Glu Gln Ala Ser Gln Glu Val Lys Asn Trp Met Thr Glu Thr<br>305 310 315 320 | | 960 |
| ttg ttg gtc caa aat gcg aac cca gat tgt aag act att tta aaa gca<br>Leu Leu Val Gln Asn Ala Asn Pro Asp Cys Lys Thr Ile Leu Lys Ala<br>325 330 335 | | 1008 |

| ttg gga cca gga gcg aca cta gaa gaa atg atg aca gca tgt cag gga | 1056 |
| Leu Gly Pro Gly Ala Thr Leu Glu Glu Met Met Thr Ala Cys Gln Gly | |
|         340                 345                 350             | |

| gtg ggg gga ccc ggc cat aaa gca aga gtt ttg gct gaa gca atg agc | 1104 |
| Val Gly Gly Pro Gly His Lys Ala Arg Val Leu Ala Glu Ala Met Ser | |
|         355                 360                 365             | |

| caa gta aca aat cca gct acc ata atg ata cag aaa ggc aat ttt agg | 1152 |
| Gln Val Thr Asn Pro Ala Thr Ile Met Ile Gln Lys Gly Asn Phe Arg | |
|         370                 375                 380             | |

| aac caa aga aag act gtt aag tgt ttc aat tgt ggc aaa gaa ggg cac | 1200 |
| Asn Gln Arg Lys Thr Val Lys Cys Phe Asn Cys Gly Lys Glu Gly His | |
| 385             390                 395                 400     | |

| ata gcc aaa aat tgc agg gcc cct agg aaa aag ggc tgt tgg aaa tgt | 1248 |
| Ile Ala Lys Asn Cys Arg Ala Pro Arg Lys Lys Gly Cys Trp Lys Cys | |
|                 405                 410                 415     | |

| gga aag gaa gga cac caa atg aaa gat tgt act gag aga cag gct aat | 1296 |
| Gly Lys Glu Gly His Gln Met Lys Asp Cys Thr Glu Arg Gln Ala Asn | |
|         420                 425                 430             | |

| ttt tta ggg aag atc tgg cct tcc cac aag gga agg cca ggg aat ttt | 1344 |
| Phe Leu Gly Lys Ile Trp Pro Ser His Lys Gly Arg Pro Gly Asn Phe | |
|         435                 440                 445             | |

| ctt cag agc aga cca gag cca aca gcc cca cca gaa gag agc ttc agg | 1392 |
| Leu Gln Ser Arg Pro Glu Pro Thr Ala Pro Pro Glu Glu Ser Phe Arg | |
| 450                 455                 460                     | |

| ttt ggg gaa gag aca aca act ccc tct cag aag cag gag ccg ata gac | 1440 |
| Phe Gly Glu Glu Thr Thr Thr Pro Ser Gln Lys Gln Glu Pro Ile Asp | |
| 465                 470                 475                 480 | |

| aag gaa ctg tat cct tta gct tcc ctc aga tca ctc ttt ggc agc gac | 1488 |
| Lys Glu Leu Tyr Pro Leu Ala Ser Leu Arg Ser Leu Phe Gly Ser Asp | |
|                 485                 490                 495     | |

| ccc tcg tca caa taa                                             | 1503 |
| Pro Ser Ser Gln                                                 | |
|         500                                                     | |

```
<210> SEQ ID NO 4
<211> LENGTH: 1503
<212> TYPE: DNA
<213> ORGANISM: Human immunodeficiency virus

<400> SEQUENCE: 4
```

| atgggtgcga gagcgtcggt attaagcggg ggagaattag ataaatggga aaaaattcgg | 60 |
| ttaagacccg ggggaaagaa acaatataaa ctaaaacata tagtatgggc aagcagagag | 120 |
| ctagaacgat tcgcagttaa tcctggcctt ttagagacat cagaaggctg tagacaaata | 180 |
| ctgggacagc tacaaccatc cgttcagaca ggatcagaag aacttagatc attatataat | 240 |
| acaatagcag tcctctattg tgtgcatcaa agaatagatg taaaagacac caaagaagcc | 300 |
| ttagataaga tagaagaaga gcaaaacaaa agtaagaaaa aagcacagca agcagcagct | 360 |
| gacacgggaa acaacagcca gtcagccaa aattaccccta gtgcagaa cctccagggg | 420 |
| caaatggtac atcaagccat atcacctaga actttaaatg catgggtaaa agtagtagaa | 480 |
| gagaaagctt tcagcccaga agtaataccc atgttttcag cattatcaga aggagccacc | 540 |
| ccacaagatt taaataccat gctaaacaca gtggggggac atcaagcagc catgcaaatg | 600 |
| ttaaaagaga ccatcaatga agaagctgca gaatgggata gattgcatcc agtgcatgcg | 660 |
| gggcctattg caccgggcca gatgagagaa ccacggggaa gtgacatagc gggaactact | 720 |
| agtacccttc aagaacaaat tggatggatg acacataatc cacctatccc agtgggagaa | 780 |
| atctataaaa gatggataat cctgggatta aataaaatag taagaatgta tagccctacc | 840 |

```
agcattctgg acataagaca aggaccaaaa gaacccttta gagactatgt agaccgattc    900
tataaaactc taagagccga gcaagcttca caagaagtaa aaaattggat gacagaaacc    960
ttgttggtcc aaaatgcgaa cccagattgt aagactattt taaaagcatt gggaccggga   1020
gcgacactag aagaaatgat gacagcatgt cagggagtgg ggggacccgg ccataaagca   1080
agagttttgg ctgaagcaat gagccaagta acaaatccag ctaccataat gatacagaag   1140
ggcaattttc ggaaccaaag aaagactgtt aagtgtttca attgtggcaa agaggggcac   1200
atagccaaaa attgccgggc ccctagaaaa aggggctgtt ggaaatgtgg aaaagaggga   1260
caccaaatga aagattgtac tgagagacaa gctaattttt tggggaagat ctggccttcc   1320
cacaagggaa gaccggggaa ttttcttcag agcagaccag agccaacagc cccaccagaa   1380
gagagcttca gatttgggga agagacaaca actccctctc agaagcggga gccgatagac   1440
aaagaactgt atcctttagc ttccctcaga tcactctttg gcagcgaccc ctcgtcacaa   1500
taa                                                                 1503
```

<210> SEQ ID NO 5
<211> LENGTH: 500
<212> TYPE: PRT
<213> ORGANISM: Human immunodeficiency virus

<400> SEQUENCE: 5

```
Met Gly Ala Arg Ala Ser Val Leu Ser Gly Gly Glu Leu Asp Lys Trp
  1               5                  10                  15

Glu Lys Ile Arg Leu Arg Pro Gly Gly Lys Lys Gln Tyr Lys Leu Lys
             20                  25                  30

His Ile Val Trp Ala Ser Arg Glu Leu Glu Arg Phe Ala Val Asn Pro
         35                  40                  45

Gly Leu Leu Glu Thr Ser Glu Gly Cys Arg Gln Ile Leu Gly Gln Leu
     50                  55                  60

Gln Pro Ser Leu Gln Thr Gly Ser Glu Glu Leu Arg Ser Leu Tyr Asn
 65                  70                  75                  80

Thr Ile Ala Val Leu Tyr Cys Val His Gln Arg Ile Asp Val Lys Asp
                 85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly Asn Asn Ser Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
                245                 250                 255
```

-continued

```
Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Pro Ala Thr Ile Met Ile Gln Lys Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500
```